(12) United States Patent
DiPerna et al.

(10) Patent No.: US 11,419,978 B2
(45) Date of Patent: Aug. 23, 2022

(54) SUBCUTANEOUS ACCESS HUB WITH MULTIPLE CANNULA PORTS

(71) Applicant: QUASURAS, INC., Escondido, CA (US)

(72) Inventors: Paul M. DiPerna, Escondido, CA (US); Marc Goldman, San Diego, CA (US)

(73) Assignee: QUASURAS, INC., Escondido, CA (US)

( * ) Notice: Subject to any disclaimer, the term of this patent is extended or adjusted under 35 U.S.C. 154(b) by 124 days.

(21) Appl. No.: 16/520,521

(22) Filed: Jul. 24, 2019

(65) Prior Publication Data

US 2020/0030529 A1 Jan. 30, 2020

Related U.S. Application Data

(60) Provisional application No. 62/703,346, filed on Jul. 25, 2018.

(51) Int. Cl.
*A61M 5/158* (2006.01)
*A61M 5/142* (2006.01)
(Continued)

(52) U.S. Cl.
CPC .......... *A61M 5/158* (2013.01); *A61K 38/28* (2013.01); *A61M 5/14248* (2013.01);
(Continued)

(58) Field of Classification Search
CPC .............. A61M 5/158; A61M 5/14248; A61M 25/0097; A61M 25/02; A61M 39/0208;
(Continued)

(56) References Cited

U.S. PATENT DOCUMENTS

| 4,594,058 A | 6/1986 | Fischell |
| 5,399,168 A | 3/1995 | Wadsworth et al. |

(Continued)

FOREIGN PATENT DOCUMENTS

| WO | WO 15/134526 | 9/2015 |
| WO | WO 17/194074 | 11/2017 |
| WO | WO 19/010324 | 1/2019 |

OTHER PUBLICATIONS

"Grip, 2011, Houghton Mifflin Harcourt Publishing Company, American Heritage® Dictionary of the English Language, Fifth Edition" (Year: 2011).*

(Continued)

*Primary Examiner* — Nilay J Shah
(74) *Attorney, Agent, or Firm* — Schmeiser, Olsen & Watts LLP

(57) ABSTRACT

Subcutaneous access hub embodiments are discussed herein that include housing embodiments having a plurality of cannula ports and a fluid passageway network that allows fluid communication between a fluid source and the plurality of cannula access ports. Such a configuration may allow a user such as a patient or clinician to releasably secure the housing to an outside surface of the patient's skin. Multiple locations on the patient's skin may then be accessed for deployment of one or more delivery cannulas via a plurality of cannula ports for delivery of fluid and from the fluid source to multiple subcutaneous locations below the patient's skin and timely movement of cannula access in the patient's skin without the need for relocating the housing.

5 Claims, 19 Drawing Sheets

(51) Int. Cl.
  *A61M 25/00* (2006.01)
  *A61M 25/02* (2006.01)
  *A61M 39/02* (2006.01)
  *A61K 38/28* (2006.01)
  *A61M 39/00* (2006.01)

(52) U.S. Cl.
  CPC ........ *A61M 25/0097* (2013.01); *A61M 25/02* (2013.01); *A61M 39/0208* (2013.01); *A61M 2005/14252* (2013.01); *A61M 2005/1586* (2013.01); *A61M 2025/0266* (2013.01); *A61M 2039/0036* (2013.01); *A61M 2039/0205* (2013.01); *A61M 2039/0223* (2013.01)

(58) Field of Classification Search
  CPC ........... A61M 2005/14252; A61M 2039/0036; A61M 2039/0205; A61M 2039/0223; A61M 2025/0266; A61M 2005/1586; A61M 2039/0211; A61M 2039/2017; A61M 2005/2411; A61K 38/28
  See application file for complete search history.

(56) References Cited

U.S. PATENT DOCUMENTS

| | | | |
|---|---|---|---|
| 5,573,515 | A | 11/1996 | Wilson et al. |
| 6,186,982 | B1 | 2/2001 | Gross et al. |
| 6,620,138 | B1 | 9/2003 | Marrgi et al. |
| 6,669,669 | B2 | 12/2003 | Flaherty et al. |
| 8,056,582 | B2 | 11/2011 | DiPerna |
| 8,167,581 | B2 | 5/2012 | Schneeberger et al. |
| 8,298,184 | B2 | 10/2012 | DiPerna et al. |
| 8,408,421 | B2 | 4/2013 | DiPerna |
| 8,448,824 | B2 | 5/2013 | DiPerna |
| 8,545,440 | B2 | 10/2013 | Patrick et al. |
| 8,573,027 | B2 | 11/2013 | Rosinko et al. |
| 8,926,561 | B2 | 1/2015 | Verhoef et al. |
| 8,986,253 | B2 | 3/2015 | DiPerna |
| 9,211,377 | B2 | 12/2015 | DiPerna et al. |
| 9,250,106 | B2 | 2/2016 | Rosinko et al. |
| 9,295,779 | B2 | 3/2016 | Kamen et al. |
| 9,295,780 | B2 | 3/2016 | Gray et al. |
| 9,339,603 | B2 | 5/2016 | Gray et al. |
| 9,901,689 | B2 | 2/2018 | Kamen et al. |
| 10,010,674 | B2 | 7/2018 | Rosinko et al. |
| 10,279,106 | B1 | 5/2019 | Cook et al. |
| 10,682,463 | B2 | 6/2020 | Kamen et al. |
| 2002/0004643 | A1 | 1/2002 | Carmel et al. |
| 2003/0204165 | A1* | 10/2003 | Houben ................ A61M 39/04 604/93.01 |
| 2004/0257413 | A1 | 12/2004 | Anderson et al. |
| 2005/0119611 | A1 | 6/2005 | Marano-Ford et al. |
| 2007/0005017 | A1* | 1/2007 | Alchas .................. A61M 5/425 604/117 |
| 2007/0078432 | A1* | 4/2007 | Halseth ................. A61M 5/158 604/500 |
| 2008/0051716 | A1 | 2/2008 | Stutz |
| 2008/0092969 | A1 | 4/2008 | DiPerna |
| 2009/0069750 | A1* | 3/2009 | Schraga ............ A61M 5/14248 604/167.02 |
| 2010/0145303 | A1 | 6/2010 | Yodfat et al. |
| 2010/0232992 | A1 | 9/2010 | Gray |
| 2011/0021993 | A1 | 1/2011 | Bar-Haim et al. |
| 2012/0130313 | A1* | 5/2012 | Byerly ............... A61B 5/15146 604/173 |
| 2013/0055889 | A1 | 3/2013 | Herz et al. |
| 2014/0378903 | A1 | 12/2014 | Quinlan |
| 2015/0273199 | A1* | 10/2015 | Adams ................ A61M 39/162 604/256 |
| 2015/0273201 | A1 | 10/2015 | Tallarida et al. |
| 2015/0290445 | A1 | 10/2015 | Powers et al. |
| 2016/0129178 | A1 | 5/2016 | Askarinya et al. |
| 2016/0361489 | A1 | 12/2016 | DiPerna |
| 2017/0128709 | A1 | 5/2017 | Chen |
| 2019/0009023 | A1 | 1/2019 | DiPerna et al. |
| 2020/0030529 | A1 | 1/2020 | Di Perna et al. |

OTHER PUBLICATIONS

"Septum, 2011, Houghton Mifflin Harcourt Publishing Company, American Heritage® Dictionary of the English Language, Fifth Edition" (Year: 2011).*
International Search Report and Written Opinion dated Oct. 4, 2019 in International Application No. PCT/US2019/43146 filed: Jul. 24, 2019.
Final Office Action dated Jun. 26, 2020 in U.S. Appl. No. 15/122,132, filed Aug. 26, 2016 and published as: 2016/0361489 on Dec. 15, 2016.
Office Action dated Jan. 2, 2020 in U.S. Appl. No. 15/122,132, filed Aug. 26, 2016 and published as: 2016/0361489 on Dec. 15, 2016.
International Search Report and Written Opinion dated Oct. 18, 2018 in International Application No. PCT/US2018/40944, filed: Jul. 5, 2018 and published as: WO/2019/010324 on Jan. 10, 2019.
International Search Report and Written Opinion dated Jul. 31, 2015 in International Application No. PCT/US2015/18525 filed: Mar. 3, 2015 and published as: WO/2015/134526 on: Sep. 11, 2015.
Office Action dated Nov. 16, 2020 in U.S. Appl. No. 16/028,256, filed Jul. 5, 2018 and published as: 2019/0009023 on Jan. 1, 2019.
International Preliminary Report on Patentability dated Jan. 26, 2021 in International Application No. PCT/US2019/43146 filed: Jul. 24, 2019.

* cited by examiner

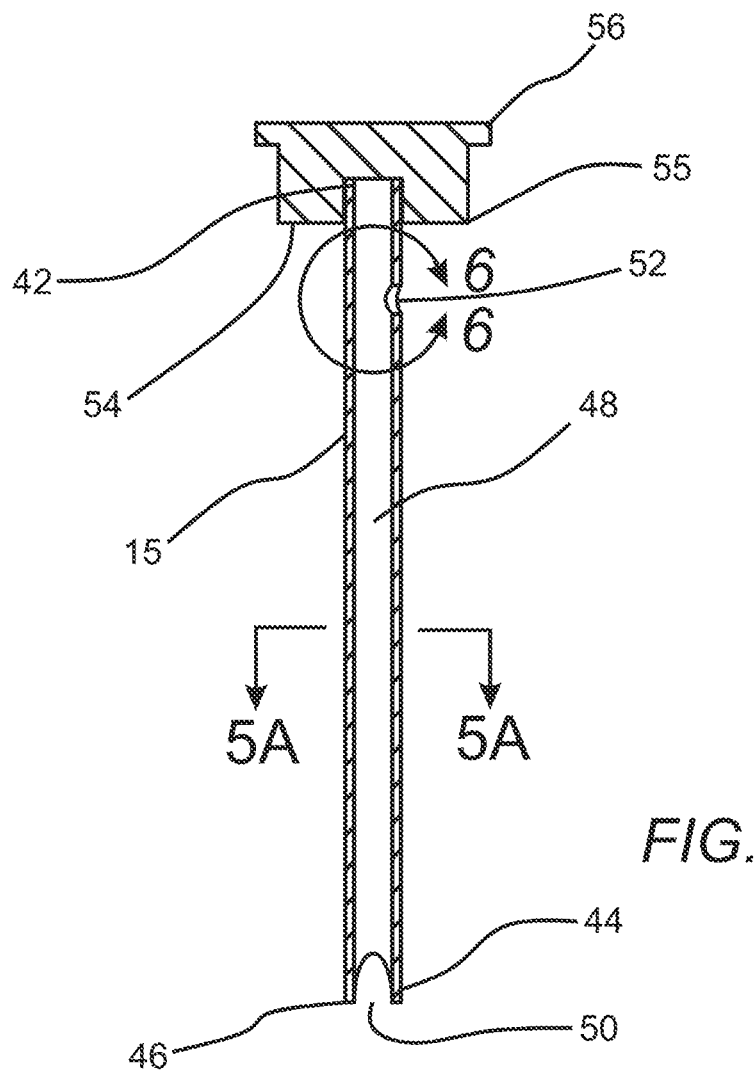
FIG. 5
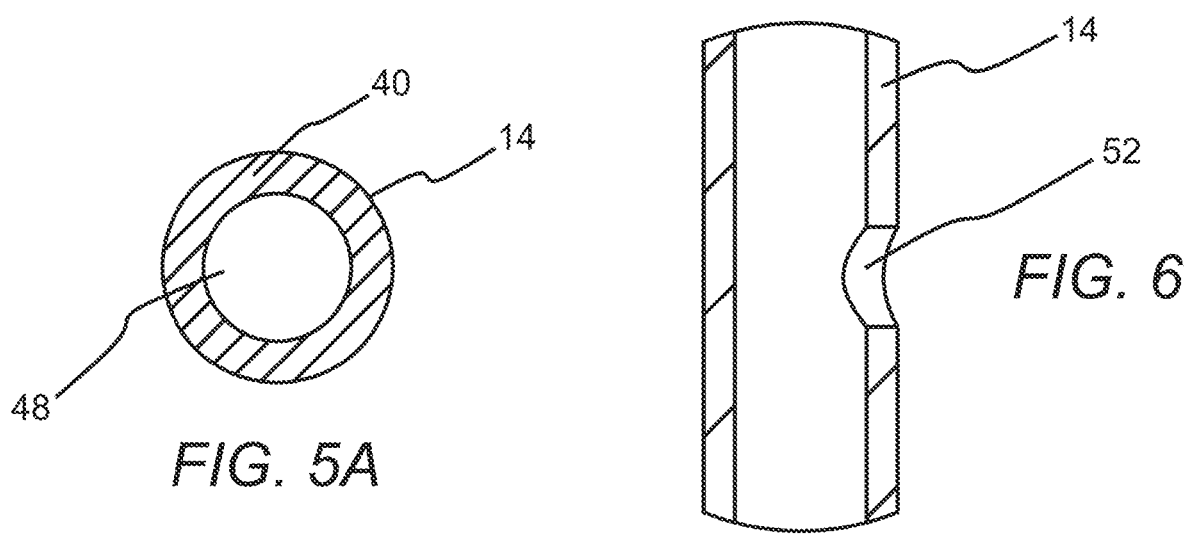
FIG. 5A
FIG. 6

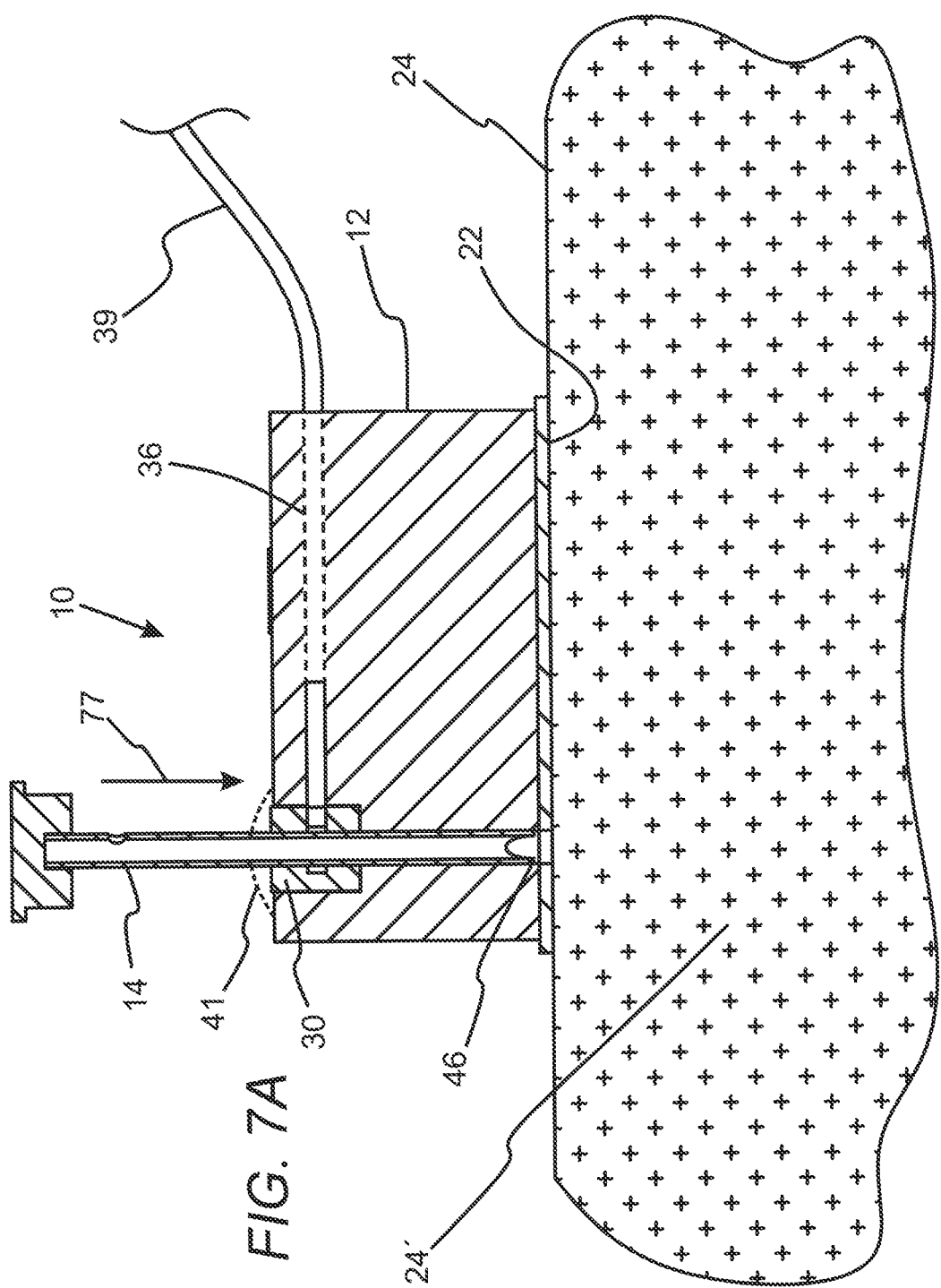

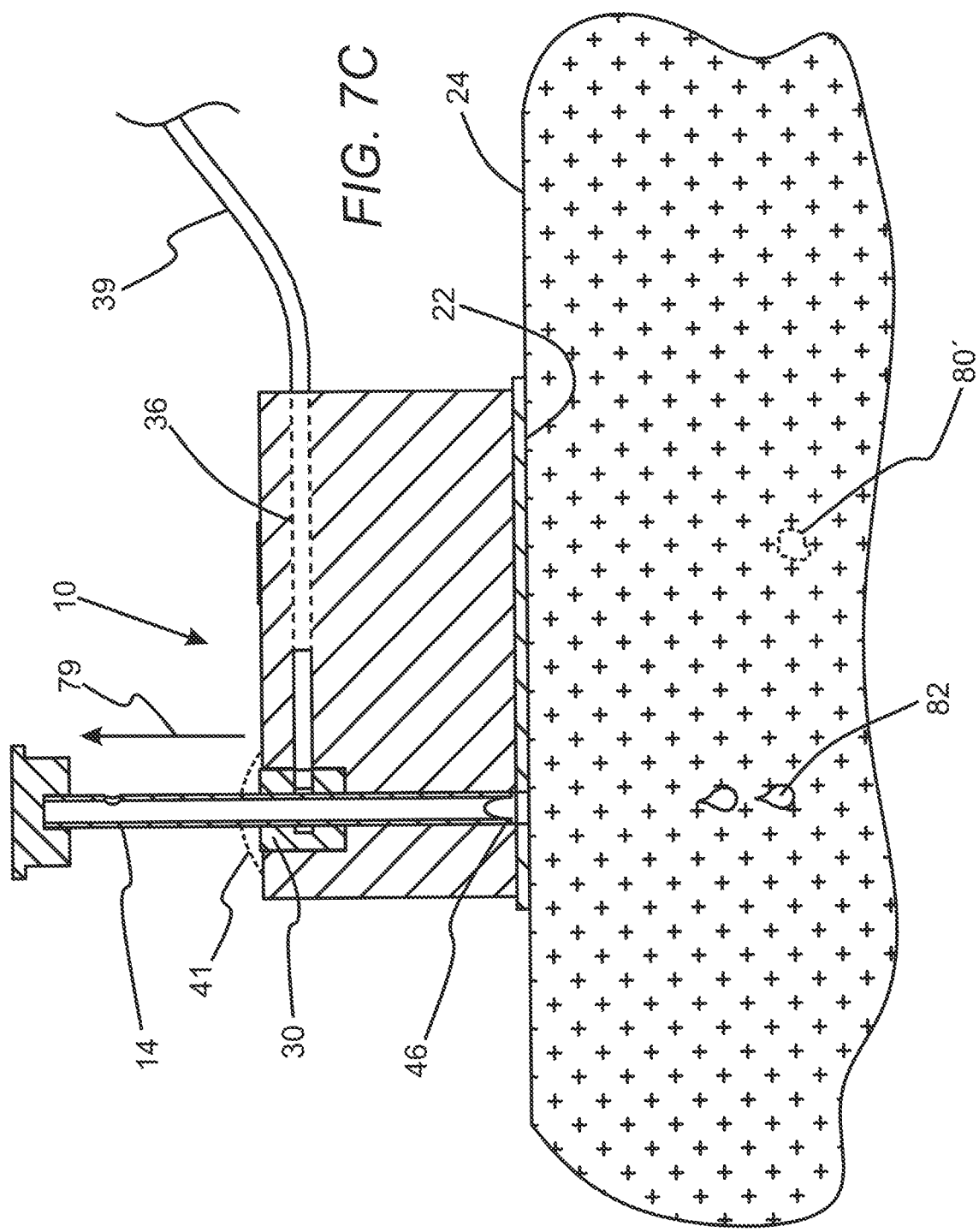

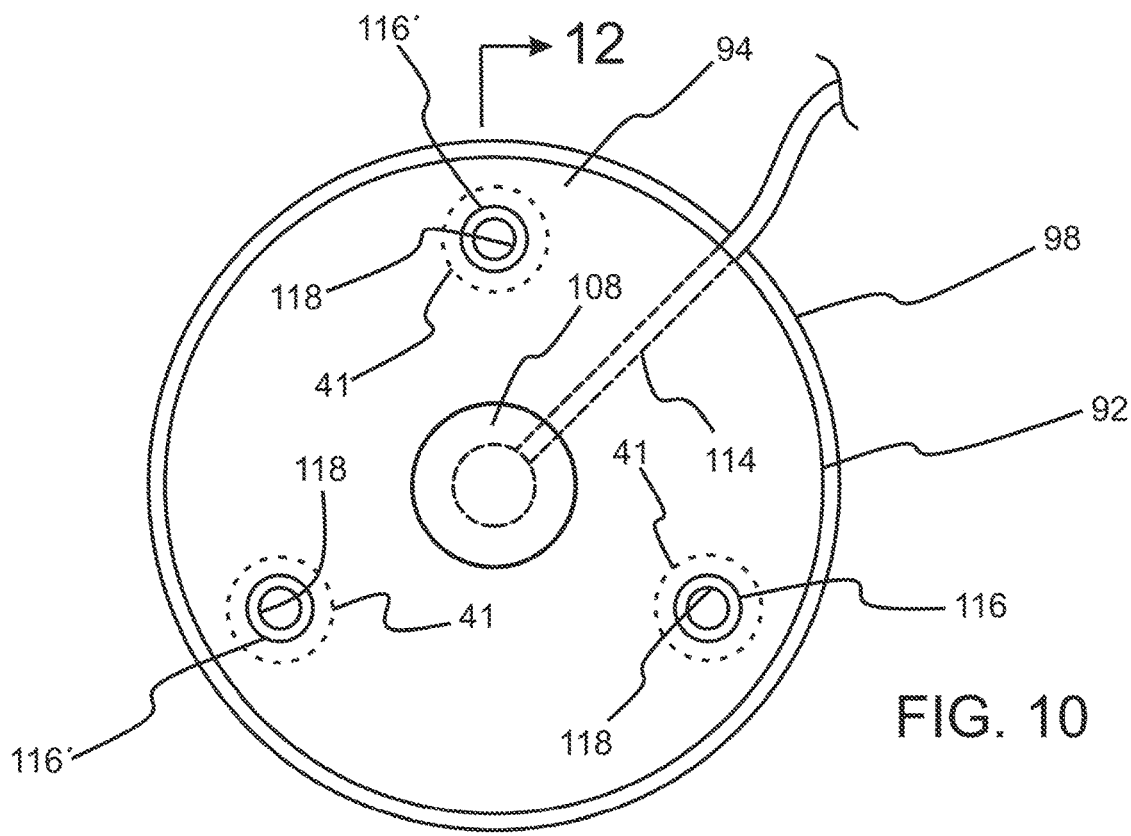
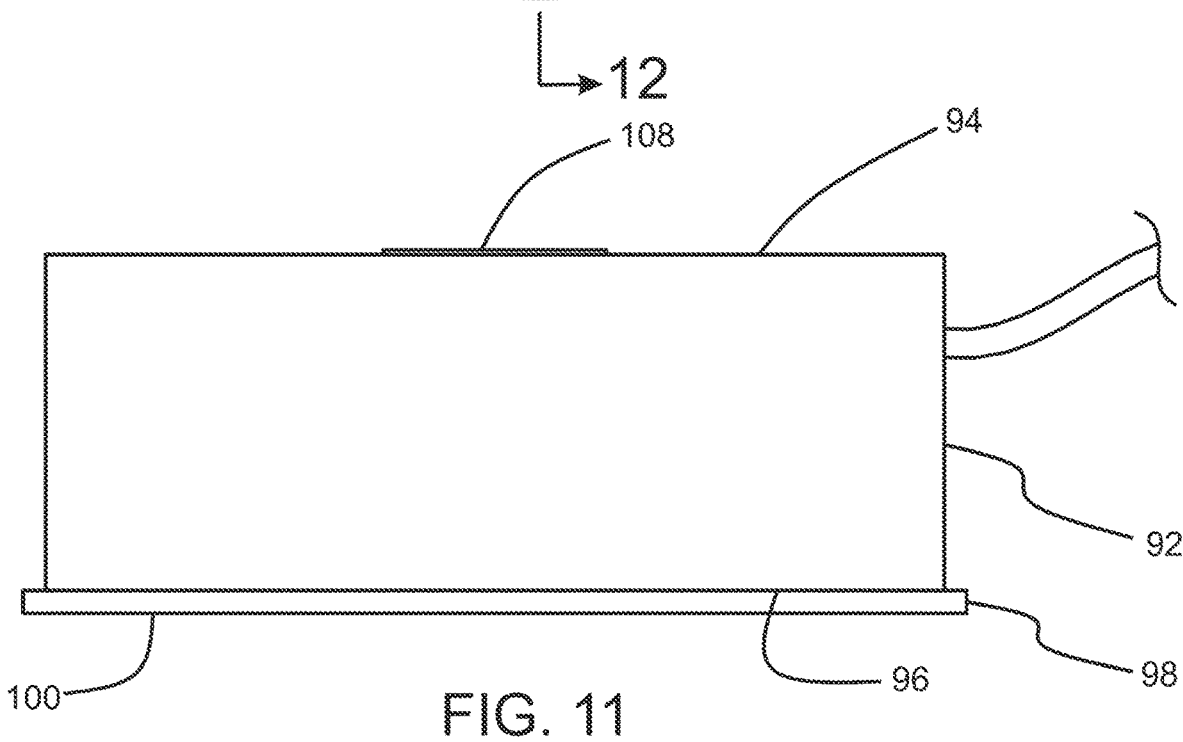

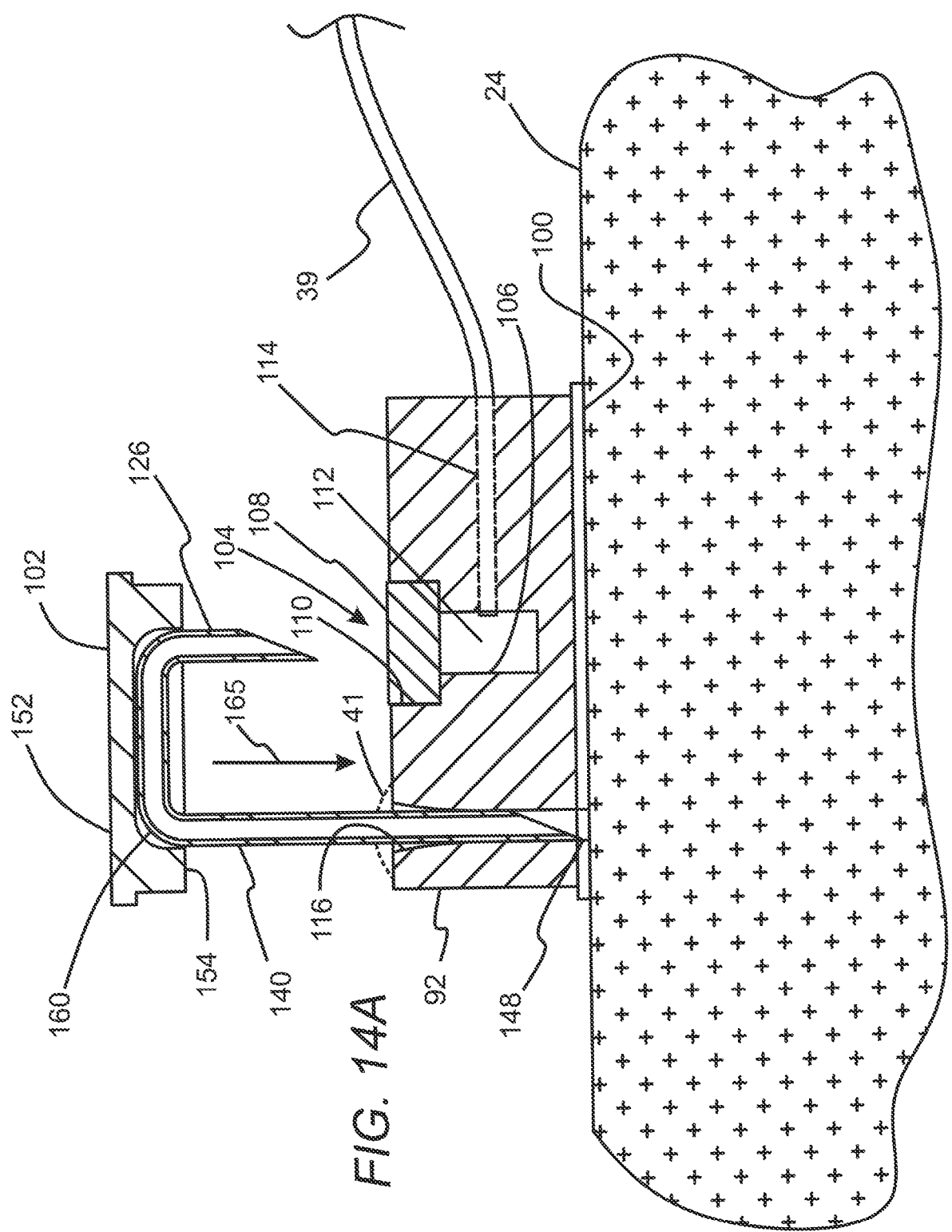

SUBCUTANEOUS ACCESS HUB WITH MULTIPLE CANNULA PORTS

RELATED APPLICATIONS

This application claims priority under 35 U.S.C. section 119(e) from U.S. Provisional Patent Application Ser. No. 62/703,346, filed on Jul. 25, 2018, by P. DiPerna titled "HUB WITH MULTIPLE INJECTION PORTS FOR EXTENDED INDWELLING", which is incorporated by reference herein in its entirety.

BACKGROUND

Many current clinical practices include changing out flexible catheters and associated needles (often referred to as cannulas) that deliver fluids including therapeutic fluids such as medicaments from a fluid source or supply, such as a pump or fluid reservoir for example, through a patient's skin to a subcutaneous location or position within the patient's body. Such changes of the catheters and associated needles are often carried out in intervals including, for example, intervals of every 3 days or so to prevent a variety of potential complications such as infection. Such catheters typically include a hypodermic type needle secured to a rigid hub. The hub may be adhered to the patient's skin with an adhesive with the tip of the needle and distal opening thereof disposed in the subcutaneous position where the therapeutic fluid will be delivered. Although this practice is often performed by clinical professionals, patients such as those with diabetes mellitus and afflictions requiring similar treatment often perform these tedious processes at home on their own due to the frequency with which they must be carried out.

Notwithstanding the tedious nature of such catheter changes, adhesives that are typically used for adhering hub assembly embodiments of such catheters to a patient's skin have been improving. Some such currently available adhesives may be rated/approved to be used for far longer than a typical needle change interval of every 3 days or so, for example. Some known adhesive embodiments used to adhere a hub assembly of an ambulatory system to a patient's skin may last as long as 14 days and more. Prior to these adhesive duration improvements, changing an access site was a necessity for multiple reasons, including removal of the associated adhesive from the patient's skin, or to prevent infection at the site, but now the concern is more focused on issues related to the interaction between the patient's skin and the cannula or cannulas deployed into the skin to a subcutaneous position.

What have been needed are subcutaneous access hub embodiments and methods of using the same that are configured to access a plurality of subcutaneous cannula positions on a patient's body while taking advantage of the extended duty cycles of adhesives that may be used to secure components of such access hub embodiments to a patient's skin.

SUMMARY

Some embodiments of a subcutaneous access hub may include a housing having an outer surface, an inner surface, and an adhesive layer which is secured to the inner surface of the housing. The adhesive layer includes a contact surface that is configured to be releasably secured to an outside surface of a patient's skin. The housing may further include a plurality of delivery cannula ports which are disposed at different positions on the housing. Each delivery cannula port may include a bore that extends from the outer surface to the inner surface of the housing, and a septum which is disposed within and sealed across an outer portion of the bore. Each septum may further include a cavity which is disposed within the septum. The housing may further include a supply passageway which is disposed on the housing and which is in fluid communication with the cavity of the septum of each of the plurality of delivery cannula ports. The subcutaneous access hub embodiment may also include one or more delivery cannulas, each having a hollow tube with an outer contour configured to slide within the bore of each of the plurality of delivery cannula ports. Each delivery cannula also includes a wall portion, a proximal end, a distal end, a sharpened tip disposed on the distal end and an inner lumen extending an axial length of the hollow tube. The delivery cannula may also have a distal port which is in fluid communication with the inner lumen and may be disposed at a distal end of the inner lumen and hollow tube. An inlet port may be disposed in fluid communication with the inner lumen and may also be disposed at a proximal portion of the hollow tube. The delivery cannula may also have an axial length sufficient for the distal port to extend below the contact surface of the adhesive layer when the inlet port is disposed in fluid communication with the cavity of the septum of the delivery cannula port.

Some embodiments of a method of accessing a plurality of subcutaneous positions on a patient may include applying a contact surface of an adhesive layer of a housing of a subcutaneous access hub to an outer surface of a patient's skin so as to releasably secure the housing to the outside surface of the patient's skin. The method may also include deploying a first delivery cannula of the subcutaneous access hub through a first delivery cannula port of a plurality of delivery cannula ports of the housing until a distal port of the delivery cannula, which is disposed at a distal end of the hollow tube, is disposed at a first subcutaneous position inward of the contact surface. In addition, for such deployment, an inlet port of the first delivery cannula, which is in fluid communication with the distal port via an inner lumen of the hollow tube, may be disposed in fluid communication with a first cavity disposed within a first septum of the first delivery cannula port. The method may further include withdrawing the first delivery cannula from the first subcutaneous position and the first delivery cannula port of the housing and then deploying a second delivery cannula of the subcutaneous access hub through a second delivery cannula port of the plurality of delivery cannula ports of the housing. The second delivery cannula may be deployed until a distal port of the second delivery cannula is disposed at a second subcutaneous position inward of the contact surface and an inlet port of the second delivery cannula is disposed in fluid communication with a second cavity disposed within a second septum of the second delivery cannula port.

Some embodiments of a subcutaneous access hub may include a housing having an outer surface, an inner surface and an adhesive layer which is disposed on the inner surface of the housing and which is configured to be releasably secured to an outside surface of a patient's skin. The housing may further include a supply cannula port which is disposed on the housing, which includes a bore that extends inwardly from the outer surface of the housing and which includes a septum disposed and sealed across an outer portion of the bore defining a cavity that is disposed in the bore inward of the septum. The housing may also include a supply passageway in fluid communication with the cavity of the supply cannula port and a plurality of delivery cannula ports. Each of the delivery cannula ports is disposed at a different position on the housing equidistant from the supply cannula port and includes a bore that extends from the outer surface to the inner surface of the housing. The subcutaneous access hub embodiment may also include one or more access cannula sets, each access cannula set including a supply cannula and a delivery cannula. The supply cannula may have a hollow tubular structure that includes a longitudinal axis, an inner lumen extending an axial length thereof, a sharpened tip disposed on a distal end thereof, and an inlet port in fluid communication with the inner lumen disposed on the distal end thereof. The delivery cannula may include a hollow tubular structure having a longitudinal axis which is substantially parallel to the longitudinal axis of the supply cannula, an inner lumen extending an axial length thereof which is in fluid communication with the inner lumen of the supply cannula, a distal port at a distal end of the delivery cannula in fluid communication with the inner lumen of the delivery cannula and a sharpened tip disposed on the distal end thereof. In some cases, the longitudinal axis of the supply cannula may be spaced from the longitudinal axis of the delivery cannula by a distance substantially equal to a separation between the supply cannula port and each of the delivery cannula ports.

Some embodiments of a method of accessing a plurality of subcutaneous positions on a patient may include applying a contact surface of an adhesive layer of a housing of a subcutaneous access hub to an outer surface of a patient's skin so as to releasably secure the housing to the outside surface of the patient's skin. Thereafter, a first delivery cannula of a first access cannula set of the subcutaneous access hub may be deployed by passing a hollow tubular structure of the first delivery cannula through a first bore of the first delivery cannula port until a distal port of the first delivery cannula is disposed at a first subcutaneous position inward of the contact surface. The method also includes deploying a supply cannula of the access cannula set such that a sharpened tip and inlet port of the supply cannula penetrates and advances through a septum and bore of a supply cannula port of the housing until an inlet port of the supply cannula is disposed in fluid communication with a cavity of the supply cannula port. Thereafter, the first delivery cannula may be withdrawn from the first subcutaneous position and the first delivery cannula port of the housing. Thereafter, a second delivery cannula of a second access cannula set may then be deployed by passing a hollow tubular structure of the second delivery cannula through a second bore of the second delivery cannula port until a distal port of the second delivery cannula is disposed at a second subcutaneous position of the patient's body inward of the contact surface.

Certain embodiments are described further in the following description, examples, claims and drawings. Features of the embodiments will become more apparent from the following detailed description when taken in conjunction with the accompanying exemplary drawings.

BRIEF DESCRIPTION OF THE DRAWINGS

FIG. 5 is a section view of the delivery cannula embodiment of FIG. 4 taken along lines 5-5 of FIG. 4.

FIG. 5A is a transverse cross section view of the delivery cannula embodiment of FIG. 5 taken along lines 5A-5A of FIG. 5.

FIG. 6 is an enlarged view of the inlet port of the delivery cannula of FIG. 5 indicated by the encircled portion 6-6 of FIG. 5.

FIGS. 7A-7C are elevation views in section that illustrate deployment of the subcutaneous access hub embodiment of FIGS. 1-6 on a patient's skin.

FIG. 10 is a top view of a housing embodiment of a subcutaneous access hub embodiment that includes a supply cannula port and three delivery cannula ports.

FIG. 11 is a side view of a housing embodiment of FIG. 10.

FIGS. 14A-14C are elevation views in section that illustrate the subcutaneous access hub embodiment of FIGS. 10-13A deployed on a patient's skin.

Figure 1:
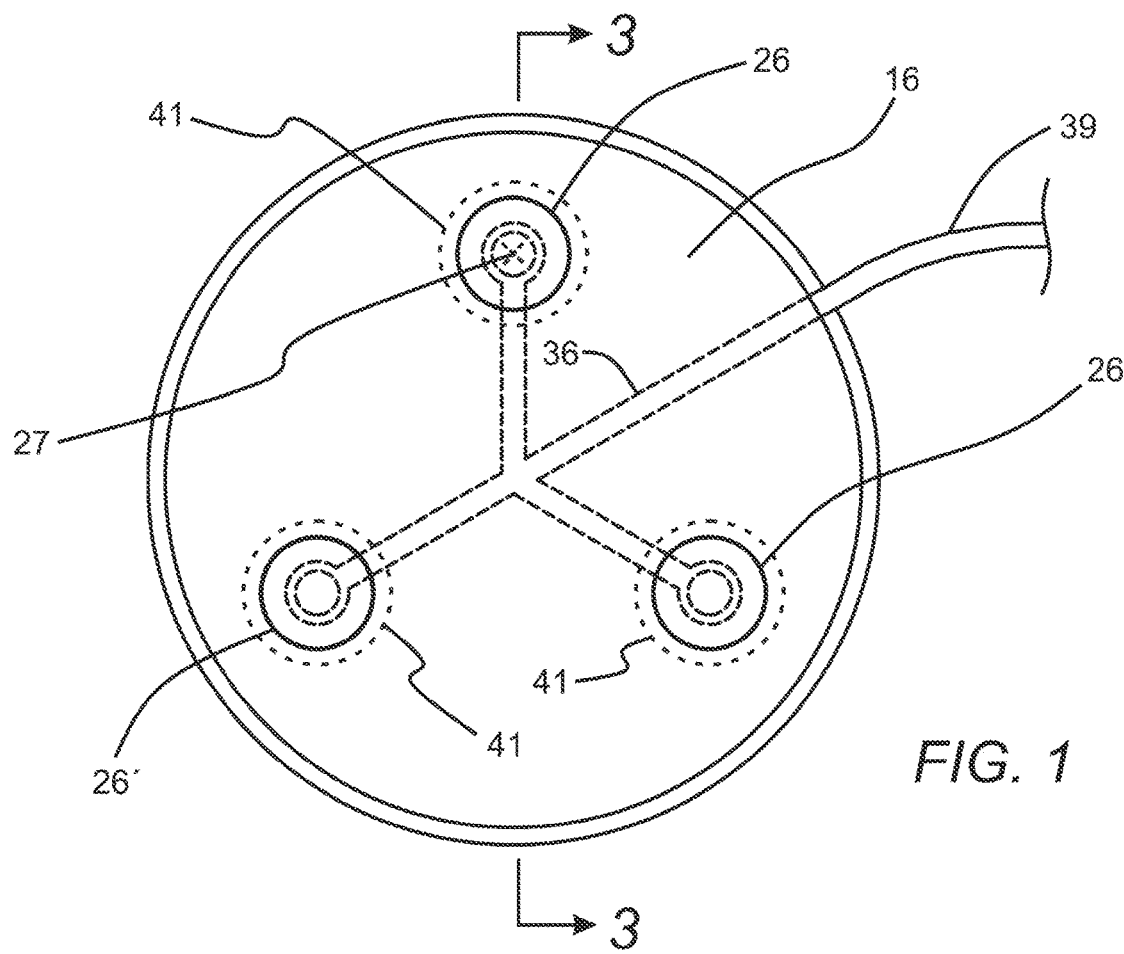
FIG. 1 is a top view of a housing embodiment of a subcutaneous access hub embodiment that includes three delivery cannula ports.

The drawings are intended to illustrate certain exemplary embodiments and are not limiting. For clarity and ease of illustration, the drawings may not be made to scale and, in some instances, various aspects may be shown exaggerated or enlarged to facilitate an understanding of particular embodiments.

DETAILED DESCRIPTION

As discussed above, many current clinical practices include changing out flexible catheters and associated needles (often referred to as cannulas) that deliver fluid from a fluid source, such as a pump or fluid reservoir for example, through a patient's skin to a subcutaneous location within the patient's body. Such changes of the catheters and associated cannulas are often carried out in intervals including every 3 days or so to prevent a variety of ailments and/or complications. Examples of complications might include infection of the cannula site or creation of scar tissue at the puncture site that may make healing of the patient's skin more difficult. Complications such as these may create issues for the patient and treating clinician so compliance with regard to this practice of catheter change out is relatively high despite being an ongoing burden and costs related to disposal of the cannula sets.

As used herein, unless noted otherwise, the term "cannula" refers to a tubular structure having an inner lumen of any desired cross section configuration through which a therapeutic fluid may be delivered. Therapeutic fluids may include any fluids that provide a benefit to a patient, including glucose solutions, saline solutions and medicaments such as insulin, antibiotics, pain medications etc. Regarding certain cannula embodiments, in some cases a cannula embodiment may include a rigid high strength structure that resists bending that may be made from a high strength material including biocompatible metallic alloys such as stainless steel, nickel titanium alloy or the like. For some cannula embodiments, the hollow tubular structure thereof may be made from a soft pliable material such as polyurethane, polytetrafluoroethylene (PTFE) including expanded PTFE and the like. For such embodiments, an inserter needle having a sharpened distal tip that extends from a distal port of the hollow tubular structure of the cannula may disposed within the inner lumen of the cannula during deployment of the cannula through a cannula port and/or a patient's tissue. Once such a cannula embodiment is deployed, the inserter needle may be proximally withdrawn from the inner lumen. In addition, as used herein, the term "subcutaneous" is being used in a broad sense that refers to any position below an outer surface of a patient's skin, including positions within the epidermis and dermis layers of the skin and below these layers of the skin of a patient.

Although this practice is typically performed by clinical professionals, patients such as those with diabetes mellitus and afflictions requiring similar treatment often struggle with this practice as well, often performing these processes at home due to the frequency with which they must be carried out. With regard to patient's suffering from diabetes, the fluid source coupled to such catheters and associated cannulas may include insulin pumps such as those discussed in commonly owned U.S. Patent Publication No. 2016/0361489, Ser. No. 15/122,132, titled "Fluid Delivery Pump", filed by P. DiPerna on Aug. 26, 2016, and U.S. Patent Publication No. 2019/0009023, Ser. No. 16/028,256, titled "Medical Pump with Flow Control," filed by P. DiPerna et al. on Jul. 5, 2018, each of which is incorporated by reference herein in its entirety.

For typical patients who are on home therapies such as insulin therapy, changing a catheter may entail a change of a fluid reservoir of an insulin pump as well. In ambulatory systems in particular, an associated catheter and fluid reservoir are often changed on the same interval. This practice often encourages/incentivizes patients to leave the catheter in longer to allow the remaining medicament to be used or to postpone the effort and cost associated with the change. Besides the cost and effort of such catheter and cannula changes, people with chronic conditions, such as diabetes, often live on an irregular recurring schedule (such as the 3-day schedule mentioned above for example) for catheter/cannula changes that does not repeat on standard days creating challenges to proper compliance.

Adhesives that are typically used for adhering housing embodiments of such catheter systems to a patient's skin have been improving over the past few years. Some such adhesives may be rated/approved to be used for far longer than a typical change interval, for example every 3 days or so. Some known adhesive embodiments such as some manufactured by companies such as 3M® and Avery® for example may be used to adhere an ambulatory system to a patient's skin may last as long as 14 days and more. Prior to these improvements in the duration of adhesive efficacy, changing an access site was a necessity for multiple reasons, including removal of the associated adhesive from the patient's skin, but now the concern is more focused on issues related to the interaction between the patient's skin and the cannula or cannulas deployed into the skin.

Discussed herein are a variety of intracorporal/subcutaneous access hub embodiments that may be used as part of an ambulatory fluid delivery system or the like. Embodiments of such intracorporal access hubs may include a housing that may remain attached to the patient's skin while providing a clinician or patient with multiple cannula port locations associated with the attached housing to choose from for deployment of a delivery cannula. In this way, the cannula may be moved to a different position or positions at any desired interval, such as every three days or so, while the housing remains attached and in place relative to the patient's body including a skin surface thereof. In some cases, a cannula may be removed from the patient's skin and discarded and a new one may be deployed into the patient's skin in a secondary alternative location relative to the patient's skin and the housing of the subcutaneous access hub embodiment. For such embodiments, plumbing such as passageways within the subcutaneous access hub may allow a desired therapeutic fluid such as a medicament to be directed from a fluid source, to the new secondary cannula location and into the patient's body.

Any of the subcutaneous access hub embodiments discussed herein may include a device attached to a patient's skin, including a device such as a patch pump, that includes a subcutaneous access hub having multiple cannula port locations. Such cannula ports may include a septum, for example, available for a cannula to pass through and into the patient's skin. The associated housing for such embodiments may plumbed or otherwise include a network of fluid passageways to allow every one of the cannula port locations to get fluid into a new and different location on the patient's skin. For some such embodiments, the cannula and hub may be configured such that the fluid only flows to the patient if there is a cannula that includes an inlet port on a side of the cannula proximal of the sharp tip, for example, that aligns with a location of a fluid passageway and/or associated cavity of the septum or other portion of a fluid passageway when the cannula is pressed through the respective septum. Additionally, there may be multiple fluid passageways to deliver a plurality of therapeutic fluids through varying cannula configurations.

Figure 2:
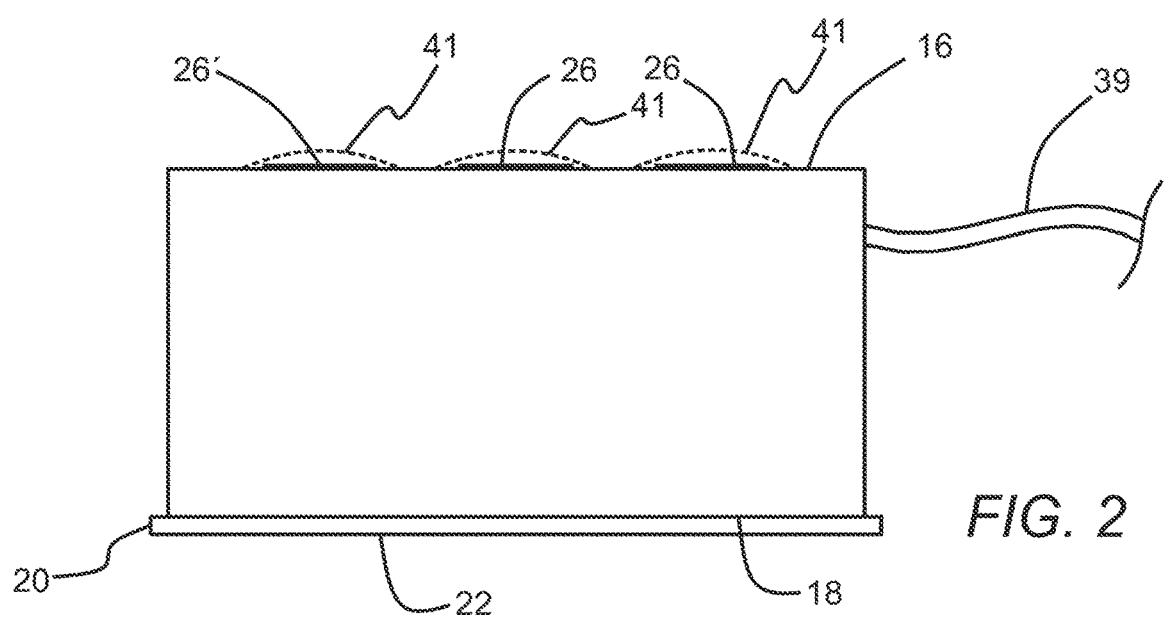
FIG. 2 is a side view of the housing of the subcutaneous access hub embodiment of FIG. 1.
Figure 2A:
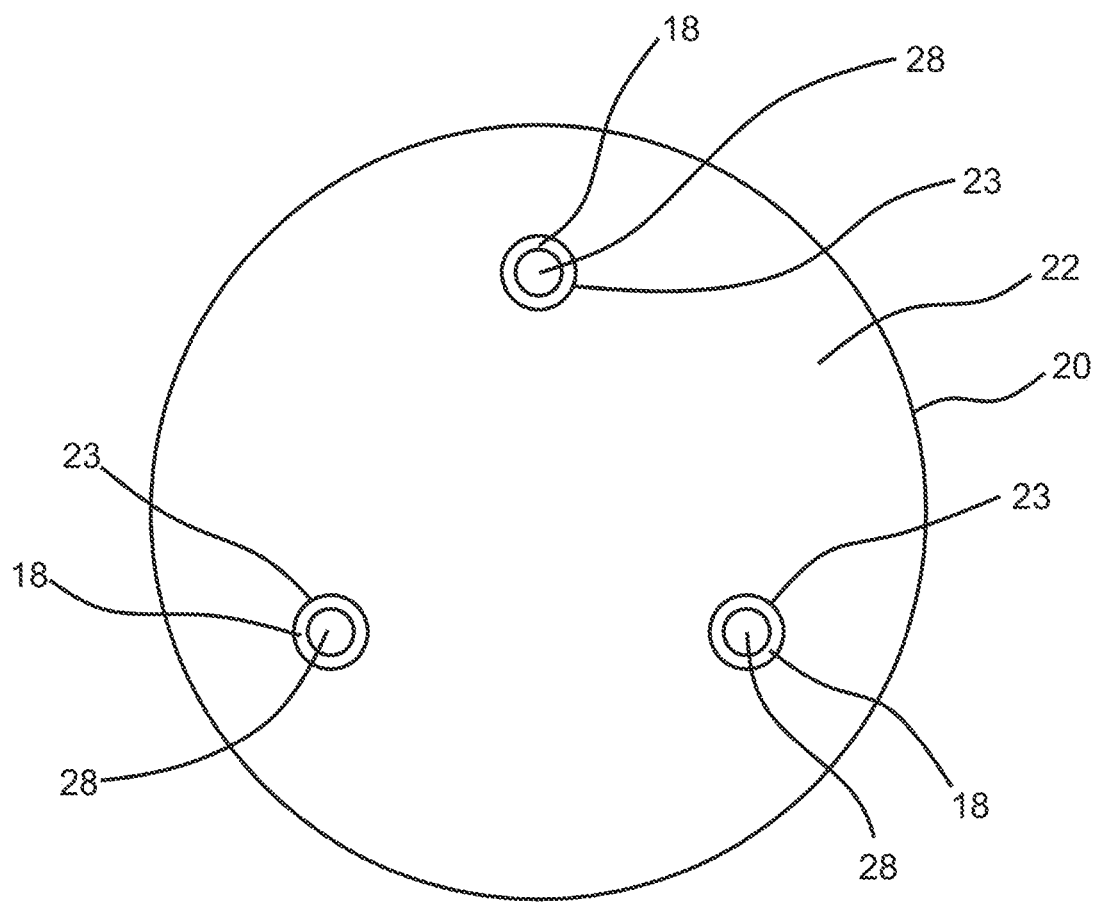
FIG. 2A is a bottom view of the housing embodiment of FIG. 1.
Figure 3:
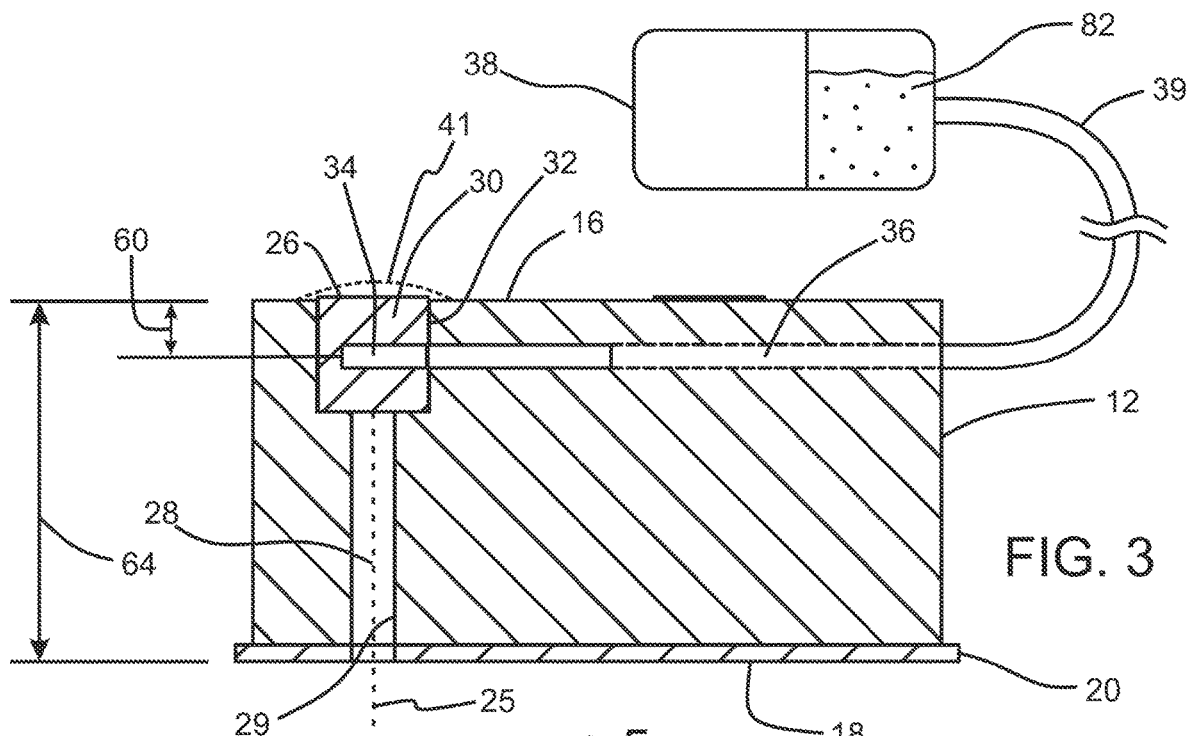
FIG. 3 is a side view of the housing of the subcutaneous access hub embodiment of FIG. 1 and a fluid source coupled in fluid communication thereto.
Figure 4:
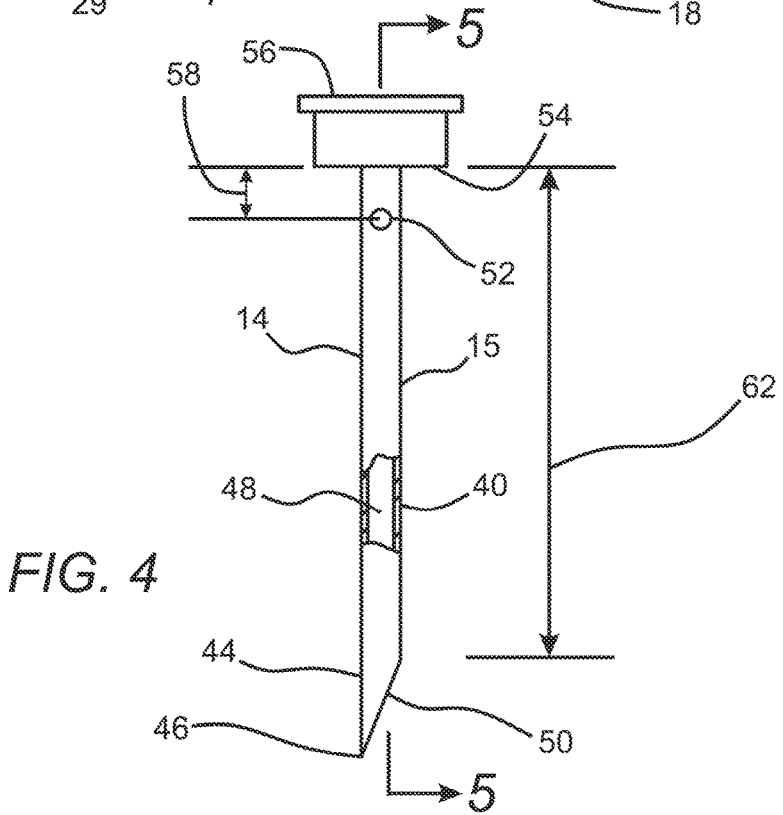
FIG. 4 is an elevation view in partial section of a delivery cannula embodiment of the subcutaneous access hub embodiment.

Referring to FIGS. 1-9, an exemplary subcutaneous access hub embodiment 10 is shown in that may include a housing 12 and a delivery cannula 14. The housing 12, as shown in FIGS. 1-3, may include an outer surface 16, an inner surface 18 disposed opposite the outer surface 16, and an adhesive layer 20 which is secured to the inner surface 18 of the housing 12. The adhesive layer 20 includes a contact surface 22 that is configured to be releasably secured to an outside surface 24 of a patient's skin as shown in the section views of FIGS. 7A-7C. In some cases, the adhesive layer 20 may include an aperture 23 as shown in FIG. 2A which is aligned with the bore 28 of each of the plurality of delivery cannula ports 26 to permit passage of the delivery cannula 14 without contacting the adhesive layer 20. In some instances, the adhesive layer may include materials such as a biocompatible acrylic with a non-woven structure or the like manufactured by a company such as 3M® or Avery®. For some embodiments, the housing 12 may have an outer transverse dimension of about 5 mm to about 20 mm, a thickness between the inner surface 18 and the outer surface 16 of about 5 mm to about 15 mm and may be made from or include rigid or semi-rigid materials that may also be biocompatible including polymers such as ABS plastic, polyvinylchloride (PVC), acrylic, nylon, polycarbonate (PC), polyethylene (PE), polyethylene terephthalate (PET), cyclic olefin copolymer (COC) as well as biocompatible alloys such as stainless steel or the like.

The housing 12 may further include a plurality of delivery cannula ports 26 which are disposed at different positions on the housing 12, with each delivery cannula port 26 including a bore 28 as shown in FIG. 3 that extends from the outer surface 16 to the inner surface 18 of the housing 12, and a septum 30 which is disposed within and sealed across an outer portion 32 of the bore 28 as shown in FIG. 3. Each septum 30 also includes a cavity 34 which is disposed within the septum 30. In some cases, the septum 30 of each of the plurality of delivery cannula ports 26 may include a resilient, elastomeric material such as rubber, polyurethane, polyisoprene, silicone or the like. In addition, for some embodiments, it may be useful to include a target mark 27 as shown in FIG. 1 disposed on an outer surface of the septum 30 in order for a user to more accurately deploy a delivery cannula 14 into the septum 30 and through the bore 28 of the delivery cannula port 26.

Figure 8:
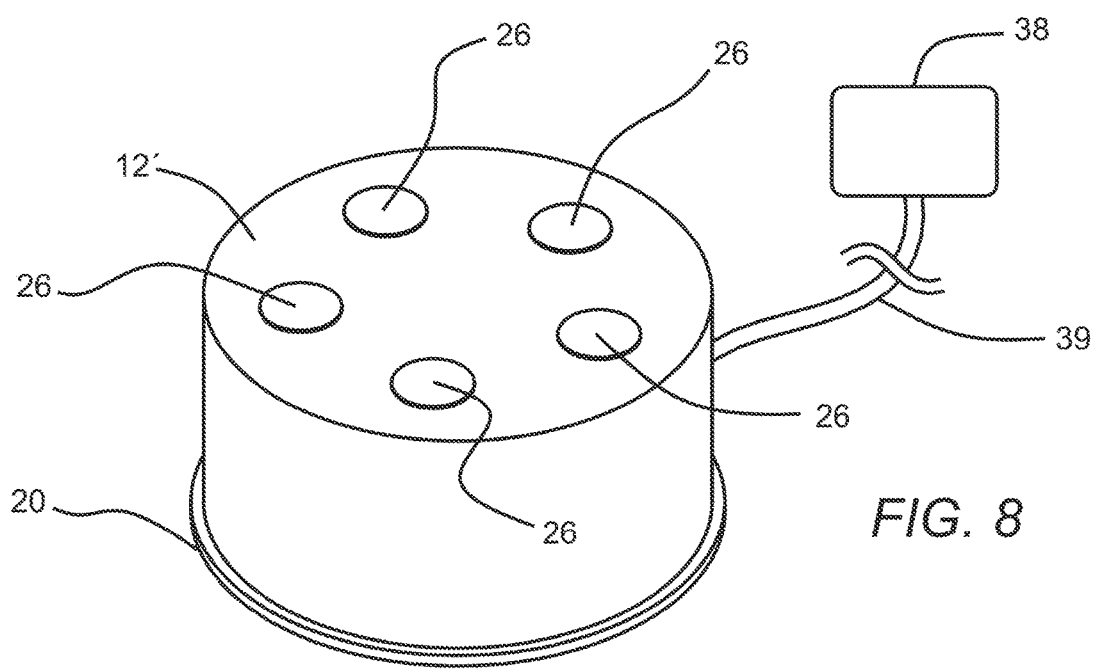
FIG. 8 is a perspective view of a housing embodiment of a subcutaneous access hub embodiment similar to the housing embodiment of FIG. 1 coupled to a fluid source and with the housing embodiment including 5 delivery cannula ports.

For some embodiments, the longitudinal axes 25 of the respective bores 28 of the plurality of delivery cannula ports 26 may be disposed substantially parallel to each other. In some cases, the longitudinal axis 25 of each bore 28 of each of the plurality of delivery cannula ports 26 may be disposed substantially perpendicular to the inner surface 18 of the housing 12. In some cases, the inner surface 18 of the housing 12 may be substantially flat or planar as may be the outer surface 16, however, any suitable contour may be used for either. In addition, any suitable number of delivery cannula ports 26 or arrangement of delivery cannula ports 26 may be used for any of the subcutaneous access hub embodiments 10 discussed herein. For example, in some cases, the housing may include about 2 delivery cannula ports to about 10 delivery cannula ports, more specifically, the housing may include about 3 delivery cannula ports to about 6 delivery cannula ports. FIG. 8 illustrates an embodiment of a housing 12' that is similar to the housing 12 discussed above that includes 5 delivery cannula ports 26 coupled in fluid communication to the fluid source 38 by the supply conduit 39.

Figure 9:
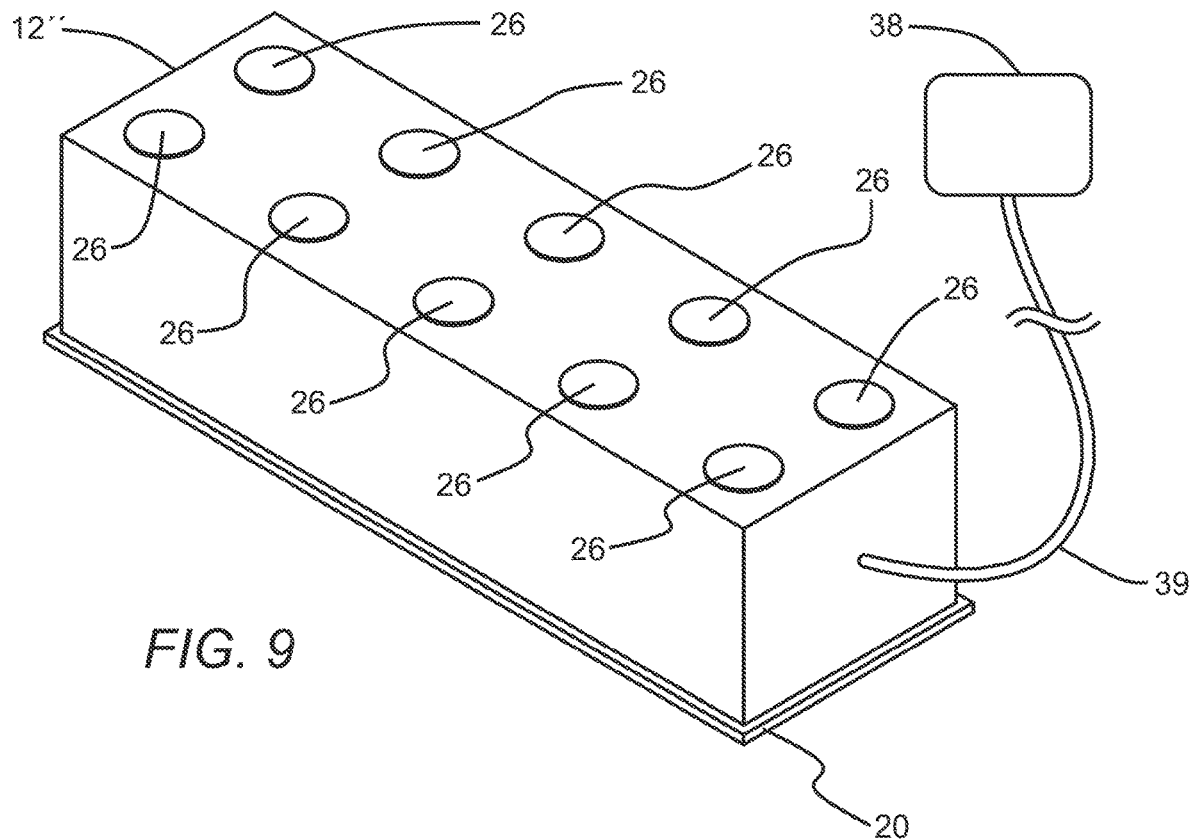
FIG. 9 is a perspective view of a housing embodiment of a subcutaneous access hub embodiment which is similar to the housing embodiment of FIG. 1, which is coupled to a fluid source and which includes a rectangular configuration with 10 delivery cannula ports.
Figure 12:
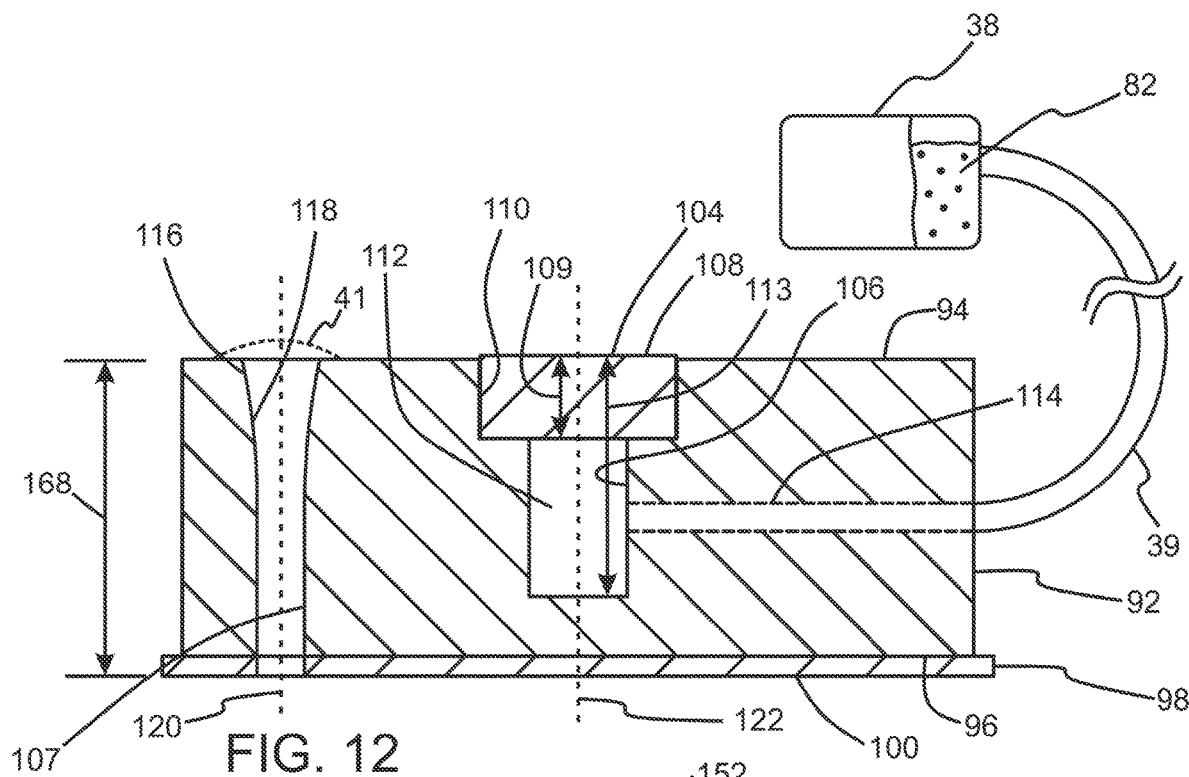
FIG. 12 is a transverse section of the housing embodiment of FIG. 10 taken along lines 12-12 of FIG. 10, with the housing shown coupled to a fluid source.
Figure 17:
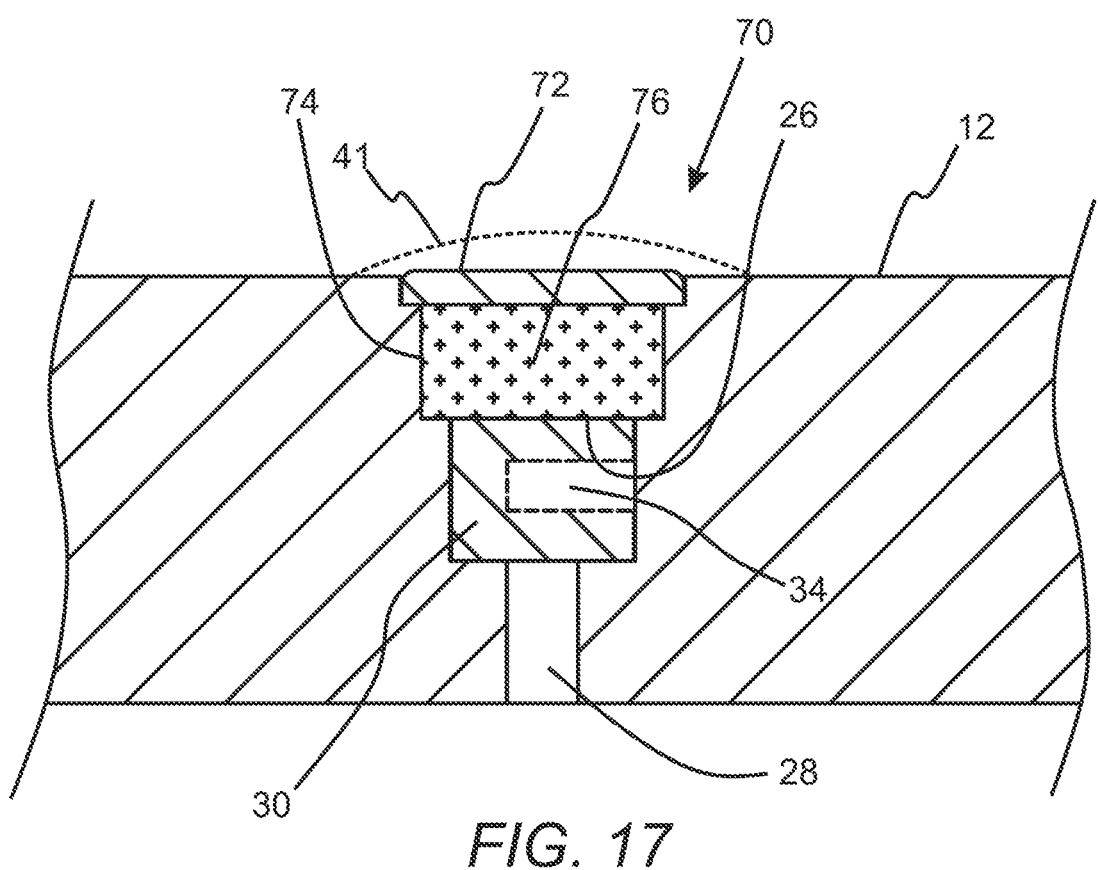
FIG. 17 is an elevation view in section of a cannula conditioner that is disposed outside of a septum of a cannula port, and that may serve as a delivery cannula conditioner, supply cannula conditioner or any other type of cannula conditioner.

In addition, the subcutaneous access hub embodiments 10 discussed herein may include a layout with a linear array which could improve integration with some systems. Such a configuration may also enable a further separation between delivery cannula ports 26 and corresponding tissue site locations. In some cases, 2 cannula ports could be placed up to 100 mm away from each other enabling a wearable patch pump device having such a subcutaneous access hub embodiment 10 incorporated into it to have separate delivery cannula ports 26 at opposite ends of such a device. In most cases, this separation adds a negligible volume to the fluid flow path due to the small cross sectional areas of the associated fluid passageways 36 and/or supply conduits 39 required for the fluid path. FIG. 9 illustrates an embodiment of a housing 12" of the subcutaneous access hub 10, similar to the housing embodiment 12 discussed above, that includes a linear type array of 10 delivery cannula ports 26 in two rows. Such a rectangular housing 12" may have a major outer transverse dimension of about 20 mm to about 150 mm, and a minor outer transverse dimension of about 10 mm to about 100 mm. Furthermore, any of the delivery cannula ports 26 discussed herein may further include an indicator 41 as shown in FIGS. 1-3 which is configured to indicate whether an delivery cannula 14 has previously penetrated the septum 30 of the delivery cannula port 26. Such optional indicators 41, as also shown in FIGS. 12, 14A and 17, may include a thin layer of non-elastic material such as a metal foil.

Figure 2B:
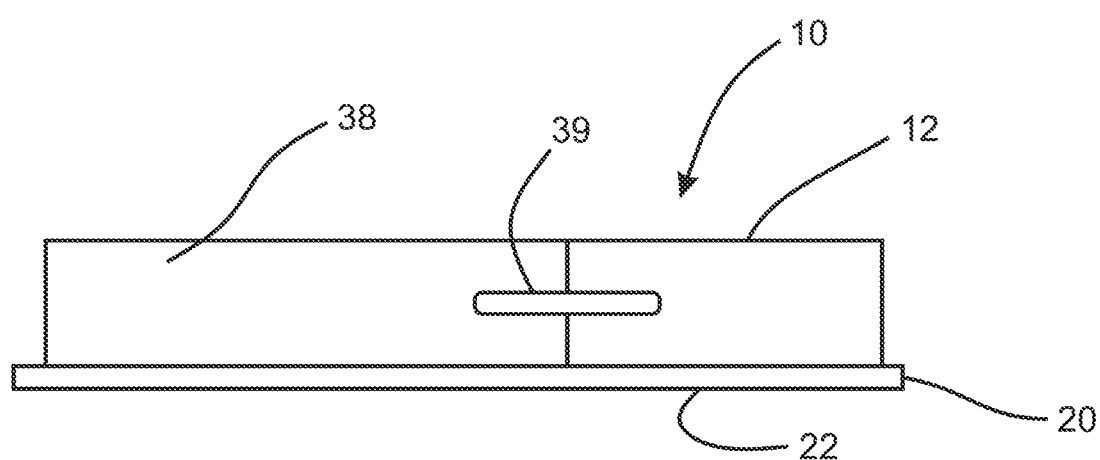
FIG. 2B is an elevation view of a subcutaneous access hub embodiment integrated with a fluid source embodiment.

As discussed above, any of the housing embodiments 12 discussed herein (including housing embodiment 90 discussed below) may be integrated with a fluid source 38 such as a pump including patch pumps for delivery of insulin or any other desirable medicament or therapeutic fluid. FIG. 2B shows an embodiment of a housing 12 of a subcutaneous access hub 10 integrated with a fluid source 38 and coupled by a supply conduit 39. The entire assembly includes an adhesive layer 20 having a contact surface 22 disposed on an inner surface thereof. The same or similar arrangement may be used for the housing embodiment 92 of the subcutaneous access hub embodiment 90 discussed below.

The housing 12 may further include a supply passageway 36 which is disposed on the housing 12 and which is in fluid communication with the cavity 34 of the septum 30 of each of the plurality of delivery cannula ports 26. In some cases, such as with the case of the embodiment of FIG. 1, the supply passageway 36 may include a network of passageways that are in fluid communication with each of the cavities 34 of the respective septums 30 of each of the delivery cannula ports 26. The supply passageway 36 may also be in fluid communication with a fluid source 38 via a supply conduit 39 which includes an inner lumen which is disposed in fluid communication between the supply passageway 36 and the fluid source 38.

The subcutaneous access hub embodiment 10 also includes the delivery cannula 14, as shown in FIGS. 4-6A, which has a hollow tube configuration with an outer contour configured to slide within the bore 28 of each of the plurality of delivery cannula ports 26. The delivery cannula 14 also has a wall portion 40, a proximal end 42, a distal end 44, and a sharpened tip 46 disposed on the distal end 44. An inner lumen 48 extends an axial length of the hollow tube, and a distal port 50 which is in fluid communication with the inner lumen 48 is disposed at a distal end of the inner lumen 48. In some instances, a transverse dimension of an outer surface 15 of the delivery cannula 14 may have a close fit with an inner surface 29 of the bore 28 of each of the plurality of delivery cannula ports 26. Such a close fit between the delivery cannula 14 and inner surface 29 of the bore 28 may be useful in some instances in order to accurately guide the delivery cannula 14 to a desired location on the patient's skin 24. In some instances, a similar result might be achieved by including additional structures on each of the delivery cannula 14 and the housing 12 (not shown) that slidably couple together and serve to accurately guide the delivery cannula 14 in substantially linear motion to a desired location on the patient's skin 24. In such cases, a close fit between the delivery cannula 14 and bore 28 might not be used as well as in any other suitable situation or embodiment. In some cases, a clearance between the outer surface 15 of the delivery cannula 14 and the inner surface 29 of the bore 28 of each of the plurality of delivery cannula ports 26 may be about 0.5 percent to about 5 percent of the transverse dimension of the delivery cannula 14, for example.

In some cases, the delivery cannula 14 also includes an inlet port 52 which is in fluid communication with the inner lumen 48 of the delivery cannula 14. The inlet port 52 may be disposed at a proximal portion of the hollow tube of the delivery cannula 14. An optional grip 56 may be disposed at the proximal end 42 of the hollow tube proximal of the inlet port 52. The grip 56 may include a stop surface 54 disposed at a distal end 55 of the grip 56. The grip 56 may be used to manually grasp the delivery cannula 14 and may also serve to define a positioning boundary for the axial position of the delivery cannula 14. As such, the inlet port 52 may be disposed distally of the stop surface 54 of the grip 56 of the delivery cannula 14 at a distance indicated by arrow 58 in FIG. 4 which may be substantially equal to (or in certain cases, greater than) a distance indicated by arrow 60 in FIG. 3 between the outer surface 16 of the housing 12 and the cavity 34 of each respective septum 30.

Figure 7B:
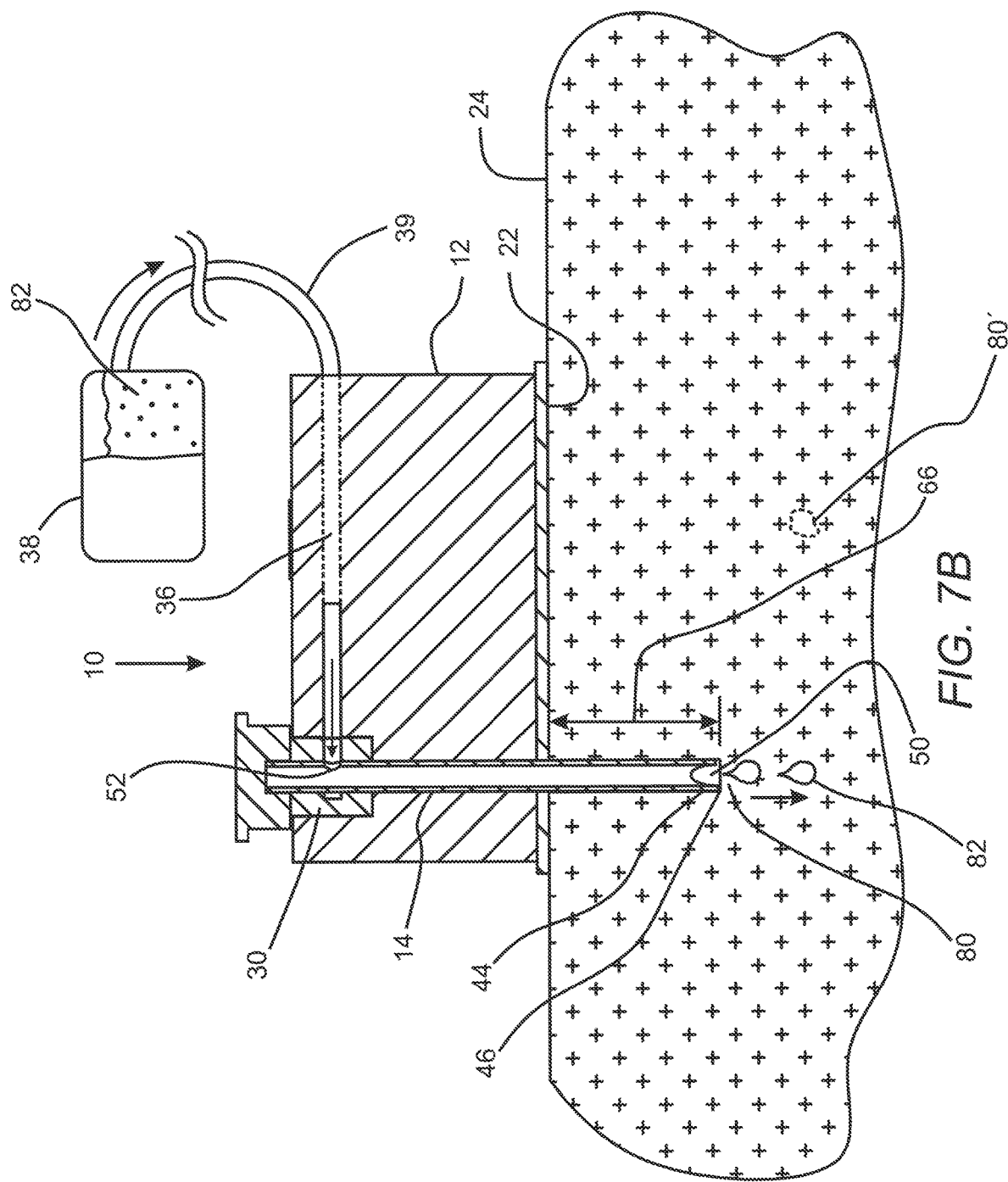

Such a configuration allows fluid communication between the cavity 34 of each septum 30 and the inlet port 52 of the delivery cannula 14 when the stop surface 54 is disposed adjacent an index surface such as the outer surface 16 of the housing for embodiments wherein distance 58 is substantially equal to distance 60 as shown in FIG. 7B. For embodiments 10 wherein the distance 58 is greater than the distance 60 (not shown), such fluid communication between the cavity 34 and the inlet port 52 may be achieved with the stop surface 54 disposed away from the outer surface 16 of the housing. In most cases, as used herein, being disposed "adjacent to" would include relative contact between surfaces or near contact between surfaces or at least within a distance corresponding to a transverse dimension of the inlet port 52 of the delivery cannula 14 in some cases. For some embodiments, the stop surface 54 associated with the delivery cannula 14 and a corresponding index surface such as the outer surface 16 associated with the housing may include any suitable structures of these respective elements so long as the respective surfaces provide a reference interaction that facilitates proper axial placement of the delivery cannula with fluid communication between the cavity 34 and inlet port 52. For example, in some cases, the index surface may include the outer surface of the septum 30 rather than the outer surface 16 of the housing itself.

The delivery cannula 14 may also have an axial length indicated by arrow 62 sufficient for the sharpened tip 46 and the distal port 50 to extend below the contact surface 22 of the adhesive layer 20 and below an outer surface of the patient's skin 24 when the stop surface 54 is disposed adjacent the outer surface 16 of the housing 12. As such, the axial length 62 of the delivery cannula 14 is greater than a distance between the outer surface 16 of the housing 12 and contact surface 22 of the adhesive layer 20 as indicated by arrow 64 in FIG. 3. In some cases, the plurality of delivery cannula ports 26 of the housing 12 and the delivery cannula 14 are configured such that the distal port 50 of the delivery cannula 14 extends to a penetration depth 66 of about 1 mm to about 8 mm from the contact surface 22 when the delivery cannula 14 is deployed within the delivery cannula port 26 with the stop surface 54 adjacent the outer surface 16 of the housing 12 as shown in FIG. 7.

Figure 6A:
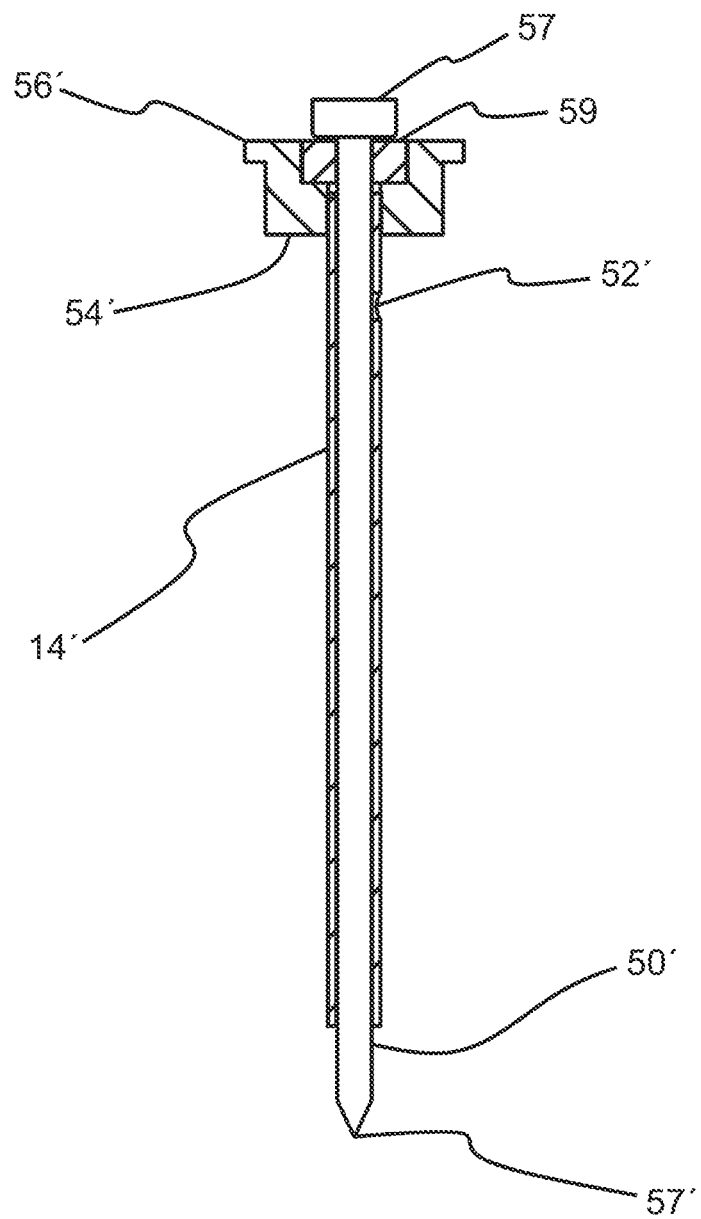
FIG. 6A is an elevation view in partial section of a delivery cannula embodiment that includes a soft pliable hollow tubular structure and an inserter needle disposed within an inner lumen thereof.

Regarding delivery cannula embodiments 14 discussed herein, in some cases the delivery cannula embodiment 14 may include a rigid high strength structure that resists bending that may be made from a high strength material including biocompatible metallic alloys such as stainless steel, nickel titanium alloy or the like. Such an embodiment may include the delivery cannula embodiment 14 of FIG. 4. In that embodiment, the sharpened tip 46 may be integrally formed from the wall material of the tubular structure of the delivery cannula 14. However, for some delivery cannula embodiments 14' as shown in FIG. 6A, the hollow tubular structure of the delivery cannula 14' may be made from a soft pliable material such as polyurethane, polytetrafluoroethylene (PTFE) including expanded PTFE or the like. For such delivery cannula embodiments 14', an inserter needle 57 having a sharpened distal tip 57' that extends from a distal port 50' of the hollow tubular structure of the delivery cannula 14' may disposed within an inner lumen of the delivery cannula 14' during deployment of the delivery cannula 14' through a delivery cannula port 26 and/or the patient's tissue 24'. Once such a delivery cannula embodiment 14' is deployed, the inserter needle 57 may be proximally withdrawn from the inner lumen of the tubular structure of the delivery cannula 14'. In order to seal a shaft of the inserter needle 57, an inserter septum 59 may be disposed at and sealed across a proximal end of the tubular structure of the delivery cannula 14'. After the inserter needle 57 has been withdrawn post deployment of the delivery cannula 14', the passage formed by the inserter needle 57 in the inserter septum 59 will self-close due to the resilient and elastic nature of the material of the septum which may include any of the materials discussed herein with regard to any septum embodiments 30, 108, including rubber, polyurethane, polyisoprene, silicone or the like. Other than withdrawal of the inserter needle 57 post deployment, the delivery cannula 14' is used in the same manner as delivery cannula embodiments 14.

Any of the subcutaneous access hub embodiments 10 discussed herein may further include an optional lock (not shown) which is configured to mechanically secure the delivery cannula 14 in a secured position relative to the housing 12 when the delivery cannula 14 is in a deployed state such as with the stop surface 54 of the grip 56 disposed adjacent the outer surface 16 of the housing 12 or with the delivery cannula 14 disposed in any other suitable axial position relative to the housing 12.

Any of the delivery cannula port embodiments 26 discussed herein (including supply cannula port embodiments 104 and delivery cannula port embodiments 116 discussed below) may include a medicament or other suitable cannula conditioning material disposed within or near the delivery cannula ports 26 that may be configured to treat the delivery cannula with a conditioning material. Such a conditioning material may include an analgesic, antiseptic, antibiotic, antimicrobial, or the like. Such a conditioning material may be used, for example, to further reduce the chance of complications and potentially numb the location of interest on the patient's skin prior to insertion of the delivery cannula 14. In some cases, the cannula conditioning material could be contained between the septum 30 of the delivery cannula port 26 and a pierceable barrier film or membrane. This may enable a user to insert a new delivery cannula 14 into a delivery cannula port 26 with little or no user preparation to the delivery cannula port 26 or delivery cannula 14.

Referring to FIG. 17, a delivery cannula conditioner 70 is disposed on the housing 12 outside of the septum 30 of each of the plurality of delivery cannula ports 26. The delivery cannula conditioner 70 shown includes an outer membrane 72, a chamber 74 disposed inside of the outer membrane 72 and a conditioning material 76 disposed in the chamber 74 between an inner surface of the outer membrane 72 and an outer surface of a septum 30 adjacent the outer membrane 72. In some instances, the conditioning material 76 may include an antibiotic, antiseptic, analgesic, alcohol wipe or the like. In addition, in some instances, each outer membrane 72 may include a target mark 27 disposed on an outer surface thereof. The target mark 27 may be useful to facilitate a user's deployment of a delivery cannula 14 into the outer membrane 72 of the delivery cannula conditioner 70 and subsequently into the bore 28 of the delivery cannula port 26 associated therewith.

Referring to FIGS. 7A-7C, some embodiments of a method of accessing a plurality of subcutaneous positions 80 on a patient may include applying the contact surface 22 of the adhesive layer 20 of the housing 12 of a subcutaneous access hub 10 to an outer surface 24 of a patient's skin so as to releasably secure the housing 12 to the outside surface 24 of the patient's skin as shown in FIG. 7A. The method may also include deploying a first delivery cannula 14 of the subcutaneous access hub 10 through a first septum 30 of a first delivery cannula port 26 of a plurality of delivery cannula ports 26 of the housing 12. The first delivery cannula 14 may be so deployed by pushing or otherwise axially translating the first delivery cannula 14 into the first delivery cannula port 26 as indicated by the inward arrow 77 shown in FIG. 7A. During deployment, the hollow tube structure of the first delivery cannula 14 is axially translated and passed through the first septum 30 and a first bore 28 of the first delivery cannula port 26 until the stop surface 54 of the grip 56 of the first delivery cannula 14 is disposed adjacent the index surface consisting of the outer surface 16 of the housing 12.

The first delivery cannula 14 may be so deployed such that the distal port 50 of the first delivery cannula 14 which is disposed at the distal end 44 of the hollow tube structure is positioned at the first subcutaneous position 80 inward of the contact surface 22 as shown in FIG. 7B. The first delivery cannula 14 is also so deployed such that the inlet port 52 of the first delivery cannula 14 (which is in fluid communication with the distal port 50 via the inner lumen 48 of the hollow tube) is disposed in fluid communication with the first cavity 34 which is disposed within the first septum 30 of the first delivery cannula port 26. In this case, the first cavity 34 is disposed in fluid communication with a supply passageway 36 of the housing 12.

For some embodiments, with such a state of deployment of the first delivery cannula 14, the distal port 50 of the delivery cannula 14 may be disposed at a penetration depth 66 of about 1 mm to about 8 mm from the contact surface 22 of the adhesive layer 20 of the housing 12 at the first subcutaneous position 80. For some embodiments, the method may further include delivering a therapeutic fluid 82 from the distal port 50 of the first delivery cannula 14 to the first subcutaneous position 80 prior to withdrawing the first delivery cannula 14 from the first subcutaneous position 80.

In some cases, delivering the therapeutic fluid 82 to the first subcutaneous position 80 includes passing the therapeutic fluid 82 from the fluid source 38, through the supply conduit 39 which is in fluid communication with the supply passageway 36 of the housing 12 as indicated by the arrow adjacent the supply conduit 39 in FIG. 7B. The therapeutic fluid is further advanced through the supply passageway 36 and into the first cavity 34 of the first septum 30, into the inlet port 50 of the first delivery cannula 14 and through the inner lumen 48 of the hollow tube of the first delivery cannula 14 as indicated by the arrow disposed within the supply passageway 36 also as shown in FIG. 7B. The therapeutic fluid is then emitted out of the distal port 50 and into the patient's tissue 24' at the first subcutaneous position 80. In some cases, the fluid source 38 includes an insulin pump and the therapeutic fluid 82 includes insulin or any other therapeutic fluid suitable for alleviating diabetes or similar ailments.

Priming an empty volume or cavity 34 of a septum embodiment 30 or associated fluid supply conduits 39 and/or supply passageways 36 after the delivery cannula 14 is inserted may be achieved in a variety of ways if so desired. A volume of air disposed within an inner lumen 48 of a delivery cannula(s) 14 being put into the body may not be a significant concern as a corresponding lack of therapeutic fluid the patient will receive during this priming process. This lack of therapeutic fluid 82 may be overcome with a prefilled delivery cannula 14 (and optionally associated supply conduits 39 and supply passageways 36) whereby the known quantity of liquid 82 is then pushed into the body until the therapeutic fluid 82 is at the distal port 50 of the delivery cannula 14 or by pushing the air into the body to fill the delivery cannula 14 so as to prevent an inadvertent dose or reducing the next dose.

The method may further include subsequently withdrawing the first delivery cannula 14 from the first subcutaneous position 80 and withdrawing the delivery cannula 14 completely from the first delivery cannula port 26 of the housing 12 after a suitable desired number of therapeutic fluid delivery cycles or time period. In some cases, the first delivery cannula 14 may be withdrawn by axially translating the first delivery cannula 14 as indicated by outward arrow 79 in FIG. 7C. A second delivery cannula 14 may then be deployed to access a second subcutaneous position 80' by passing the sharpened tip 46 of the second delivery cannula 14 of the subcutaneous access hub 10 through a second septum 30 of a second delivery cannula port 26' of the plurality of delivery cannula ports 26 of the housing 12. The deployment sequence embodiment of the second delivery cannula 14 may involve the same or similar processes and components as those used for the deployment of the first delivery cannula 14. As such, reference is made to the same FIGS. 7A-7C for illustration of the deployment sequence of the second delivery cannula 14. The second delivery cannula 14 may then be further deployed by passing the hollow tube structure of the second delivery cannula 14 through the second septum 30 and a second bore 28 of the second delivery cannula port 26' until the stop surface 54 of the grip 56 of the delivery cannula 14 is disposed adjacent the outer surface 16 of the housing 12. The second delivery cannula 14 may further be so deployed such that the distal port 50 of the second delivery cannula 14 is disposed at a second subcutaneous position 80' inward of the contact surface 22 of the adhesive layer 20 of the housing 12. In this position, the inlet port 52 of the second delivery cannula 14 is disposed in fluid communication with a second cavity 34 disposed within the second septum 30 of the second delivery cannula port 26'. Once again, the second cavity 34 may also be disposed in fluid communication with the supply passageway 36 of the housing 12.

In some instances, the second delivery cannula 14 is so deployed by axially translating the second delivery cannula 14 until the stop surface 54 of the grip 56 is disposed adjacent the index surface consisting of the outer surface 16 of the housing 12. For some embodiments, with such a state of deployment of the second delivery cannula 14, the distal port 50 of the second delivery cannula 14 may be disposed at a penetration depth 66 of about 1 mm to about 8 mm from the contact surface 22 of the adhesive layer 20 of the housing 12 at the second subcutaneous position 80'. For some embodiments, the method may further include delivering the therapeutic fluid 82 from the distal port 50 of the second delivery cannula 14 to the second subcutaneous position 80' prior to withdrawing the second delivery cannula 14 from the second subcutaneous position 80' or at any other suitable time.

In some cases, delivering the therapeutic fluid 82 to the second subcutaneous position 80' includes passing the therapeutic fluid 82 from the fluid source 38, through the supply conduit 39 which is in fluid communication with the supply passageway 36 of the housing 12. The therapeutic fluid is further advanced through the supply passageway 36 and into the second cavity 34 of the second septum 30, into the inlet port 50 of the second delivery cannula 14 and through the inner lumen 48 of the hollow tube of the second delivery cannula 14. The therapeutic fluid 82 is then emitted out of the distal port 50 of the second delivery cannula 14 and into the patient's tissue at the second subcutaneous position 80'. In some cases, the fluid source 38 includes an insulin pump and the therapeutic fluid 82 includes insulin or any other therapeutic fluid suitable for alleviating diabetes or similar ailments. Although it may be possible in some cases to reuse the same delivery cannula 14 for subsequent deployment into a second different delivery cannula port 26 after deployment into a first delivery cannula port 26, most often a new unused second delivery cannula 14 will be used for deployment at a new secondary site. As such, the subcutaneous access hub embodiments 10 discussed herein may include a plurality of delivery cannulas 14 including about 2 delivery cannulas 14 to about 20 delivery cannulas 14 or more.

Some subcutaneous access hub embodiments may include the use of an access cannula set with two cannulas, one for pressing through a first septum that is disposed adjacent a cavity in fluid communication with a supply passageway and a second hole in the housing whereby the second cannula may be aligned with and pass through the second hole into the skin. The two cannulas may be secured relative to each other and in fluid communication with each other with a fluid channel disposed between and in fluid communication with respective inner lumens of the two cannulas. In addition, a similar result may be achieved with a single cannula whereby the plumbing in the form of a fluid conduit configuration allows the fluid to enter the top of the cannula, with flexible tubing, for example, prior to entering the skin. FIGS. 10-16 illustrate an embodiment of a subcutaneous access hub 90 that includes two cannulas.

Referring to FIGS. 10-16, the subcutaneous access hub embodiment 90 may include a housing 92 having an outer surface 94, an inner surface 96 disposed opposite the outer surface 94 and an adhesive layer 98 which is disposed on the inner surface 96 of the housing 92. The adhesive layer 98 includes a contact surface 100 that is configured to be releasably secured to the outside surface 24 of the patient's skin. In some instances, the adhesive layer 98 may include materials such as biocompatible acrylic with non-woven structure or the like. The subcutaneous access hub 90 further includes an access cannula set 102 that is shown in a deployed state engaged with respective cannula ports of the housing 92 in FIG. 14B. The housing 92 includes a supply cannula port 104 as shown in FIG. 12 which may be disposed on the housing 92 and which includes a bore 106 that extends inwardly from the outer surface 94 of the housing 92. The supply cannula port 104 also includes a septum 108 which is disposed and sealed across an outer portion 110 of the bore 106 defining a cavity 112 which is disposed in the bore 106 inwardly of the septum 108.

The housing 92 may also include a supply passageway 114 in fluid communication with the cavity 112 of the supply cannula port 104. In some cases, the septum 108 of the supply cannula port 104 may include a resilient, elastomeric material such as rubber, polyurethane, polyisoprene, silicone or the like. In addition, for some embodiments, it may be useful to include a target mark 27, such as the target mark 27 shown in FIG. 1 and discussed above, disposed on an outer surface of the septum 108 in order for a user to more accurately deploy a supply cannula 126 into the septum 108 and through the bore 106 of the supply cannula port 104. Furthermore, any of the supply cannula port embodiments 104 discussed herein may further include an indicator 41 which is configured to indicate whether a supply cannula 126 (discussed below) has previously penetrated the septum 108 of the supply cannula port 104.

Figure 15:
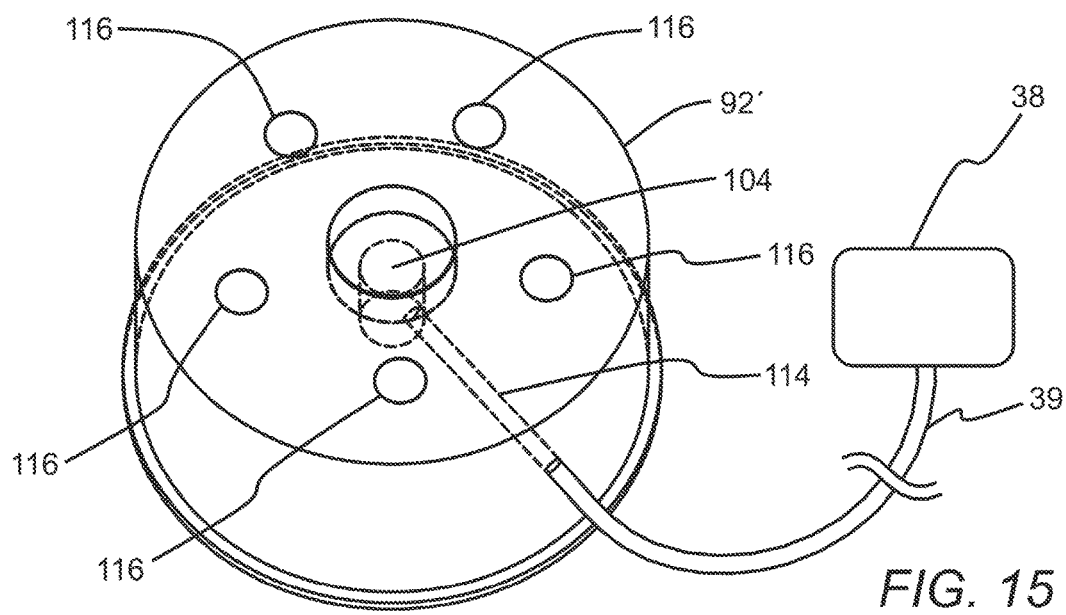
FIG. 15 is a perspective view of a housing embodiment of a subcutaneous access hub embodiment similar to the housing embodiment of FIG. 10 coupled to a fluid source and with the housing embodiment including 5 delivery cannula ports.

The housing 92 also includes a plurality of delivery cannula ports 116 which are each disposed at different positions on the housing 92 and which may be optionally disposed equidistant from the supply cannula port 104. The delivery cannula ports 116 each include a bore 118 that extends from the outer surface 94 of the housing 92 to the inner surface 96 of the housing 92 with a longitudinal axis 120 that may optionally be disposed parallel to a longitudinal axis 122 of the bore 106 of the supply cannula port 104. The longitudinal axes 120 of the respective bores 118 of the plurality of delivery cannula ports 116 may also optionally be disposed substantially parallel to each other in some cases. These longitudinal axes 120 of the bores 118 of the respective plurality of delivery cannula ports 116 may, in addition, be disposed substantially perpendicular to the inner surface 96 of the housing 92. In some cases, the housing 92 may include about 2 delivery cannula ports to about 10 delivery cannula ports, more specifically, about 3 delivery cannula ports to about 6 delivery cannula ports. FIG. 15 illustrates an embodiment of a housing 92' that is similar to the housing 92 discussed above but that includes 5 delivery cannula ports 116 which may be coupled in fluid communication to the fluid source 38 by the supply conduit 39 once an access cannula set 102 has been deployed within respective cannula ports 104, 116.

In addition, the subcutaneous access hub embodiments 90 discussed herein may include a layout with a linear array which could improve integration with some systems. Such a configuration may also enable a further separation between delivery cannula ports 116 and corresponding tissue site locations on a patient's skin 24. In some cases, 2 delivery cannula ports 116 could be placed up to 100 mm away from each other enabling a wearable patch pump device having such a subcutaneous access hub embodiment 90 incorporated into it to have separate delivery cannula ports 26 at opposite ends of such a device. This separation may add a negligible volume to the fluid flow path due to the small cross sectional areas of the associated fluid supply passageways 114 and/or supply conduits 39 required for the fluid path.

Figure 11A:
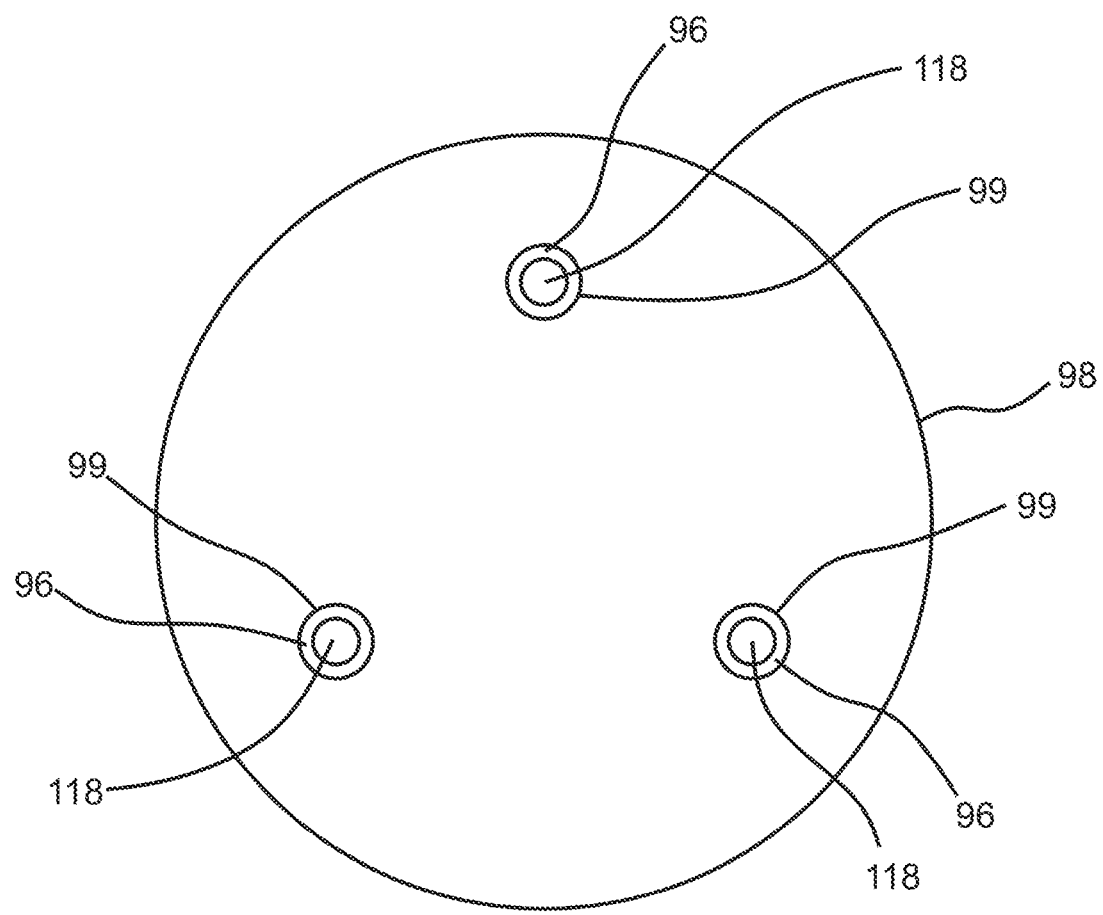
FIG. 11A is a bottom view of the housing embodiment of FIG. 10.
Figure 16:
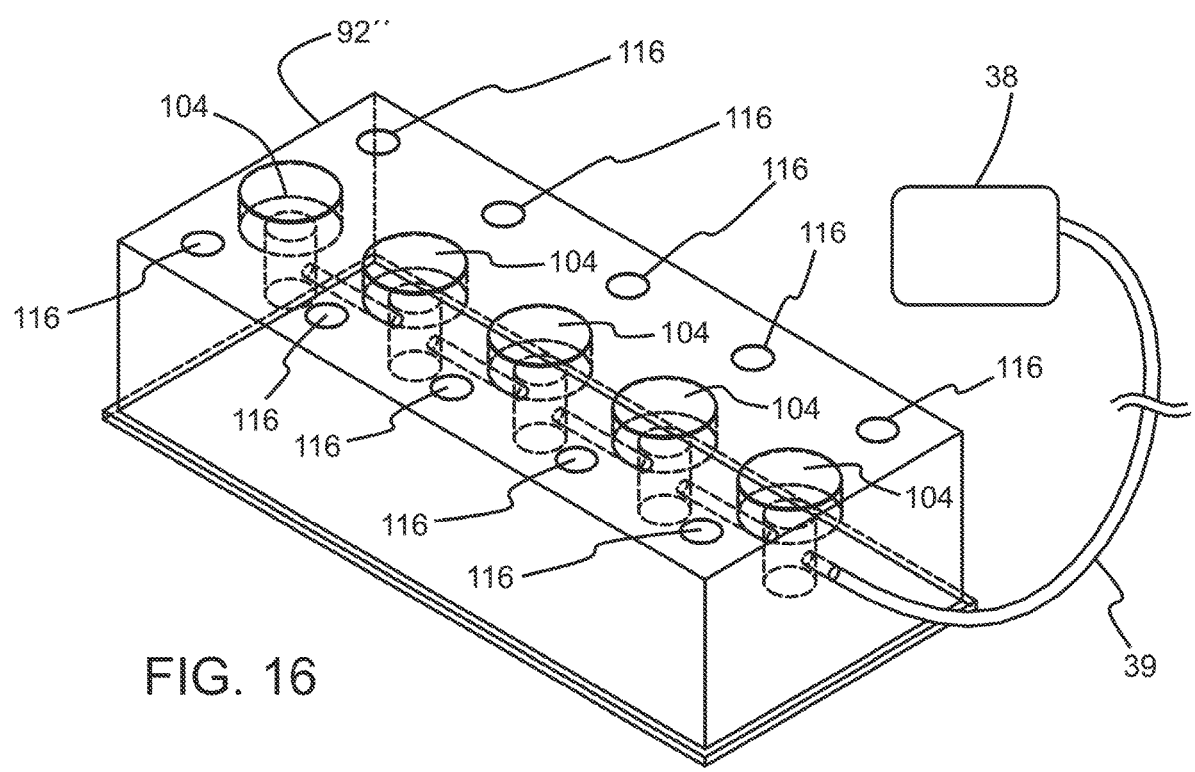
FIG. 16 is a perspective view of a housing embodiment of a subcutaneous access hub embodiment which is similar to the housing embodiment of FIG. 10, which is coupled to a fluid source and which includes a rectangular configuration with 10 delivery cannula ports.

FIG. 16 illustrates an embodiment of a housing 92" of the subcutaneous access hub 90, similar to the housing embodiment 92 discussed above, that includes a linear type array of 10 delivery cannula ports 116 disposed in two rows. Such a rectangular housing 92" may have a major outer transverse dimension of about 20 mm to about 150 mm, and a minor outer transverse dimension of about 10 mm to about 100 mm for some embodiments. Furthermore, any of the delivery cannula ports 116 discussed herein may further include an indicator 41 which is configured to indicate whether a delivery cannula 140 has previously been deployed in the delivery cannula ports 116. With regard to the cannula port configuration, in some cases, the adhesive layer 98 may include an aperture 99 as shown in FIG. 11A which is aligned with the bore 118 of each of the plurality of delivery cannula ports 116 to permit passage of the delivery cannula 140 without the delivery cannula 140 contacting the adhesive layer 98.

Referring to FIG. 17, a delivery cannula conditioner 70 is shown disposed on the housing 12 outside of the septum 30 of each of the plurality of delivery cannula ports 26. The delivery cannula conditioner 70 shown includes an outer membrane 72, a chamber 74 disposed inside of the outer membrane 72 and a conditioning material 76 disposed in the chamber 74 between an inner surface of the outer membrane 72 and an outer surface of a septum 30 adjacent the outer membrane 72. In some instances, the conditioning material 76 may include an antibiotic, antiseptic, analgesic, antimicrobial, alcohol wipe, or the like. Such a cannula conditioner 70 may be used in conjunction with any of the supply cannula port embodiments 104 or delivery cannula port embodiments 116 discussed herein for the purposes discussed above or for any other suitable purpose.

Figure 13:
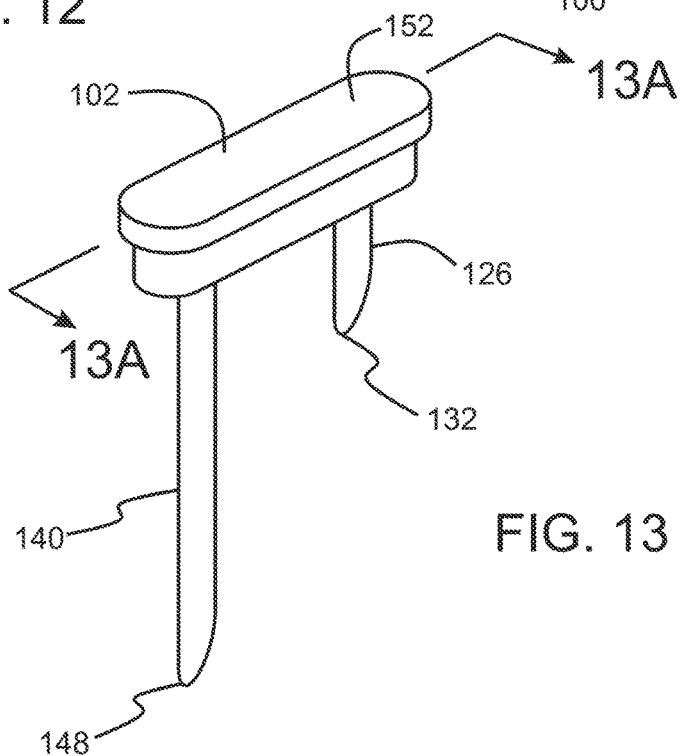
FIG. 13 is a perspective view of an access cannula set embodiment for use with the housing embodiment of FIG. 10 of the associated subcutaneous access hub embodiment.
Figure 13A:
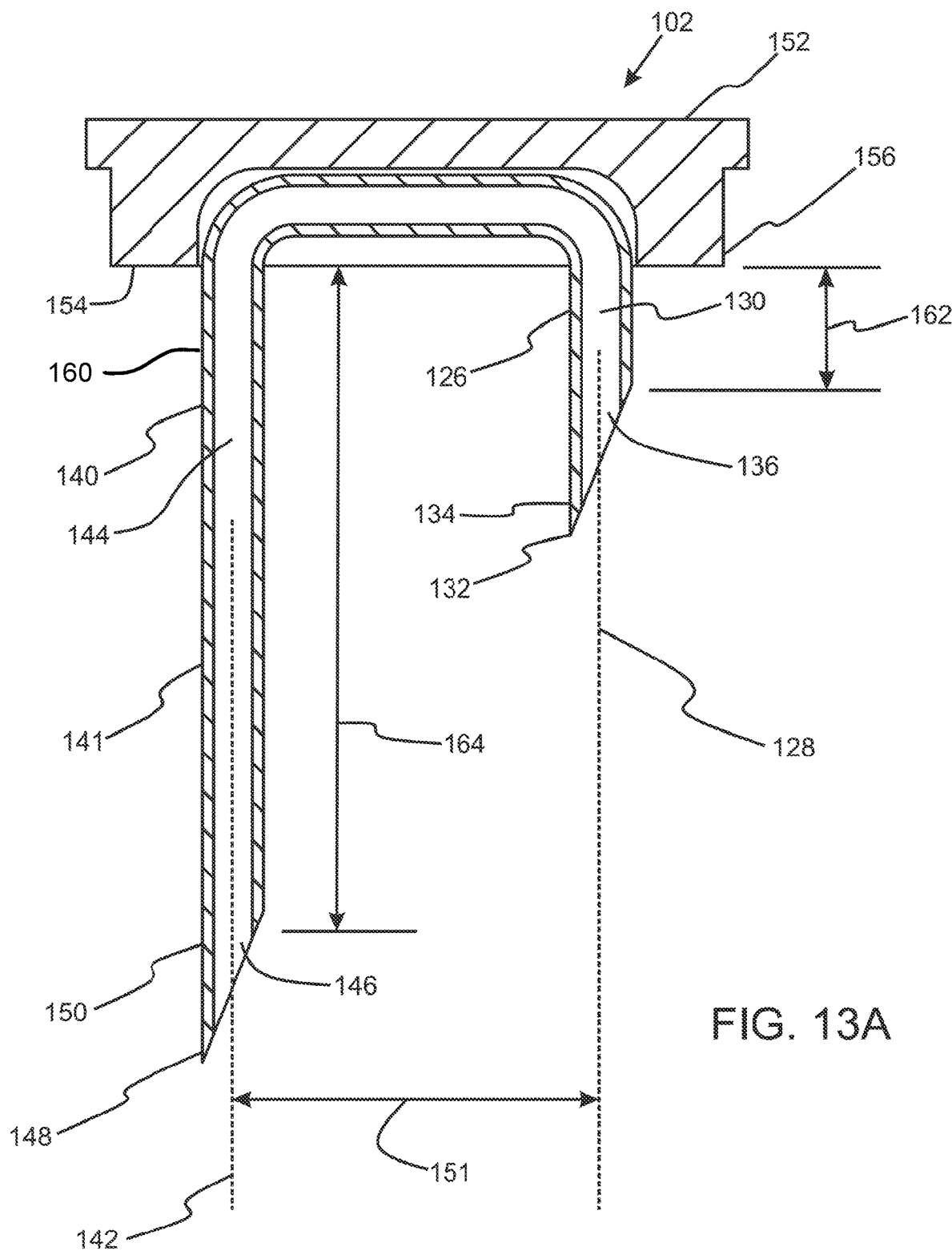
FIG. 13A is an elevation view in section of the access cannula set of FIG. 13 taken along lines 13A-13A of FIG. 13.

The subcutaneous access hub embodiment 90 also includes one or more access cannula sets 102 as shown in FIG. 13A. The access cannula set embodiment 102 includes the supply cannula 126 with a straight hollow tubular structure that includes a longitudinal axis 128, an inner lumen 130 extending and axial length thereof, a sharpened tip 132 disposed on a distal end 134 thereof, and an inlet port 136 in fluid communication with the inner lumen 130 disposed on the distal end 134 thereof. The access cannula set 102 may further include the delivery cannula 140 which has a straight hollow tubular structure with a longitudinal axis 142. The longitudinal axis 142 may optionally be disposed substantially parallel to the longitudinal axis 128 of the supply cannula 126. The delivery cannula 140 may also have an inner lumen 144 extending an axial length thereof which is in fluid communication with the inner lumen 130 of the supply cannula 126. The delivery cannula 140 also includes a distal port 146 and a sharpened tip 148 disposed at a distal end 150 of the delivery cannula 140. The distal port 146 is in fluid communication with the inner lumen 144 of the delivery cannula 140.

In some instances, a transverse dimension of an outer surface 141 of the delivery cannula 140 may have a close fit with an inner surface 107 of the bore 106 of each of the plurality of delivery cannula ports 116. As discussed above, such a close fit between the delivery cannula 140 and inner surface 107 of the bore 106 may be useful in some instances in order to accurately guide the delivery cannula 140 to a desired location on the patient's skin 24. In some instances, a similar result might be achieved by including additional structures (not shown) on each of the delivery cannula 140 and the housing 92 that slidably couple together and serve to accurately guide the delivery cannula 140 in substantially linear motion to a desired location on the patient's skin 24. In such cases, a close fit between the delivery cannula 140 and bore 106 might not be used as well as in any other suitable situation or embodiment. In some cases, a clearance between the outer surface 141 of the delivery cannula 140 and the inner surface 107 of the bore 106 of each of the plurality of delivery cannula ports 116 may be about 0.5 percent to about 5 percent of the transverse dimension of the delivery cannula 140.

For some embodiments, the longitudinal axis 128 of the supply cannula 126 may be spaced from the longitudinal axis 142 of the delivery cannula 140 by a distance indicated by arrow 151 in FIG. 13A that is substantially equal to a separation between the longitudinal axis 122 of the supply cannula port 104 and the respective longitudinal axes 120 of each of the delivery cannula ports 116 as shown in FIG. 12. Such a configuration may be useful to facilitate deployment of the delivery cannula 140 into one of the plurality of delivery cannula ports 116 simultaneously with deployment of the supply cannula 126 into the supply cannula port 104. The access cannula set 102 may also have a grip 152 secured to the supply cannula 126 and the delivery cannula 140 which may also be useful in facilitating such simultaneous deployment of the delivery cannula 140 and supply cannula 126. In some instances, the grip 152 may include a rigid body that has a stop surface 154 at an inner end 156 of the grip 152. The grip 152 may be secured to the supply cannula 126 and the delivery cannula 140 such that the hollow tubular structure of the delivery cannula 140 is secured in fixed relation to the hollow tubular structure of the supply cannula 126.

In general, with the access cannula set 102 disposed in a deployed state with the stop surface 154 of the grip 152 disposed adjacent an index surface, such as the outer surface 94 of the housing, the inlet port 136 of the supply cannula will be in fluid communication with the cavity 112 of the supply cannula port 104 and the distal port 146 of the delivery cannula 140 will be extending inward from the contact surface 100 of the adhesive layer 98 and into a desired subcutaneous location within the patient's skin 24. However, for some embodiments, the stop surface 154 associated with the access cannula set 102 and a corresponding index surface such as the outer surface 94 associated with the housing 92 may include any suitable structures of these respective elements so long as the respective surfaces provide a reference interaction that facilitates proper axial placement of the distal port 146 of the delivery cannula 140 and proper axial placement of the inlet port 136 of the supply cannula 126 with fluid communication between the inlet port 136 and cavity 112 when in a deployed state. For example, in some cases, the index surface generally associated with the housing 92 may include an outer surface of the septum 108 of the supply cannula port 104 (or any other suitable structure that is in fixed relation to the rigid structure of the housing 92) rather than the outer surface 94 of the housing 92 itself.

In addition, with regard to the embodiment shown in FIG. 13A, the supply cannula 126 and delivery cannula 140 of the access cannula set 102 may optionally both be formed together from a single continuous length of hollow tubing 160 that may include a high strength resilient material such as stainless steel, nickel titanium alloy, or the like. In addition, any of the subcutaneous access hub embodiments 90 discussed herein may further include an optional lock (not shown) which is configured to mechanically secure the access cannula set 102 in a secured position relative to the housing 92 when the access cannula set 102 is in a deployed state with the stop surface 154 of the grip 152 disposed adjacent the outer surface 94 of the housing 92 or with the supply cannula 126 and delivery cannula 140 disposed in any other suitable axial position relative to the housing 92.

Figure 14B:
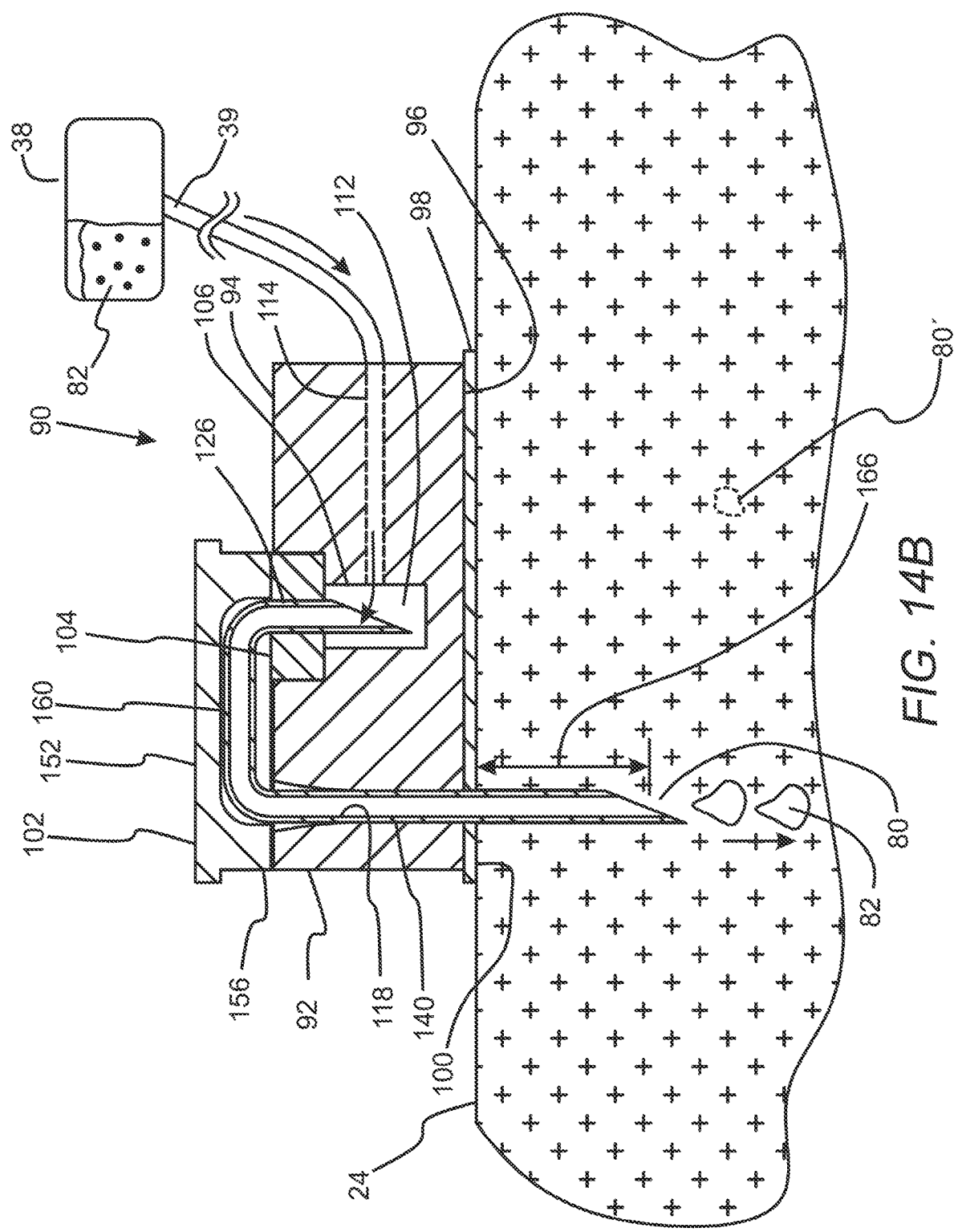

In some cases, an axial length indicated by arrow 162 in FIG. 13A of the supply cannula 126 that extends from the stop surface 154 to the inlet port 136 may be sufficient for the sharpened tip 132 and the inlet port 136 thereof to be disposed in fluid communication with the cavity 112 of the supply cannula port 104 when the stop surface 154 is disposed adjacent the outer surface 94 of the housing 92 as shown in FIG. 14B. For such an arrangement of fluid communication, the axial length 162 of the supply cannula 126 may configured so as to be greater than a thickness of the septum 108 of the supply cannula port 104 as indicated by arrow 109 shown in FIG. 12 but less than a depth of the cavity 112 as indicated by arrow 113 also shown in FIG. 12.

In addition, in some instances, an axial length of the delivery cannula 140 indicated by arrow 164 as shown in FIG. 13A from the stop surface 154 to the distal port 146 may be sufficient for the sharpened tip 148 and the distal port 146 thereof to be extended below the contact surface 100 of the adhesive layer 98 when the stop surface 154 is disposed adjacent the outer surface 94 of the housing 92. For some embodiments, a length of the plurality of distal ports 146 of the housing 92 indicated by arrow 168 in FIG. 12 and the length 164 of the delivery cannula 140 may be configured such that the distal port 146 of the delivery cannula 140 extends to a penetration depth 166 as shown in FIG. 14B of about 1 mm to about 8 mm from the contact surface 100 when the delivery cannula 140 is disposed within the delivery cannula port 116 with the stop surface 154 disposed adjacent the outer surface 94 of the housing 92.

It should be noted that the length 168 of the delivery cannula port embodiments 116 shown in FIG. 12 may, in some cases, correspond to a thickness of the housing 92 between the outer surface 94 and inner surface 96 thereof. For some embodiments, the housing 92 may have an outer transverse dimension of 5 mm to 20 mm, a thickness between the inner surface 96 and the outer surface 94 of about 5 mm to about 15 mm and may be made from or include rigid or semi-rigid materials including polymers such as ABS plastic, PVC, acrylic, nylon, PET, PE, PC, COC and biocompatible high strength alloys such as stainless steel, nickel titanium alloy or the like.

Figure 13B:
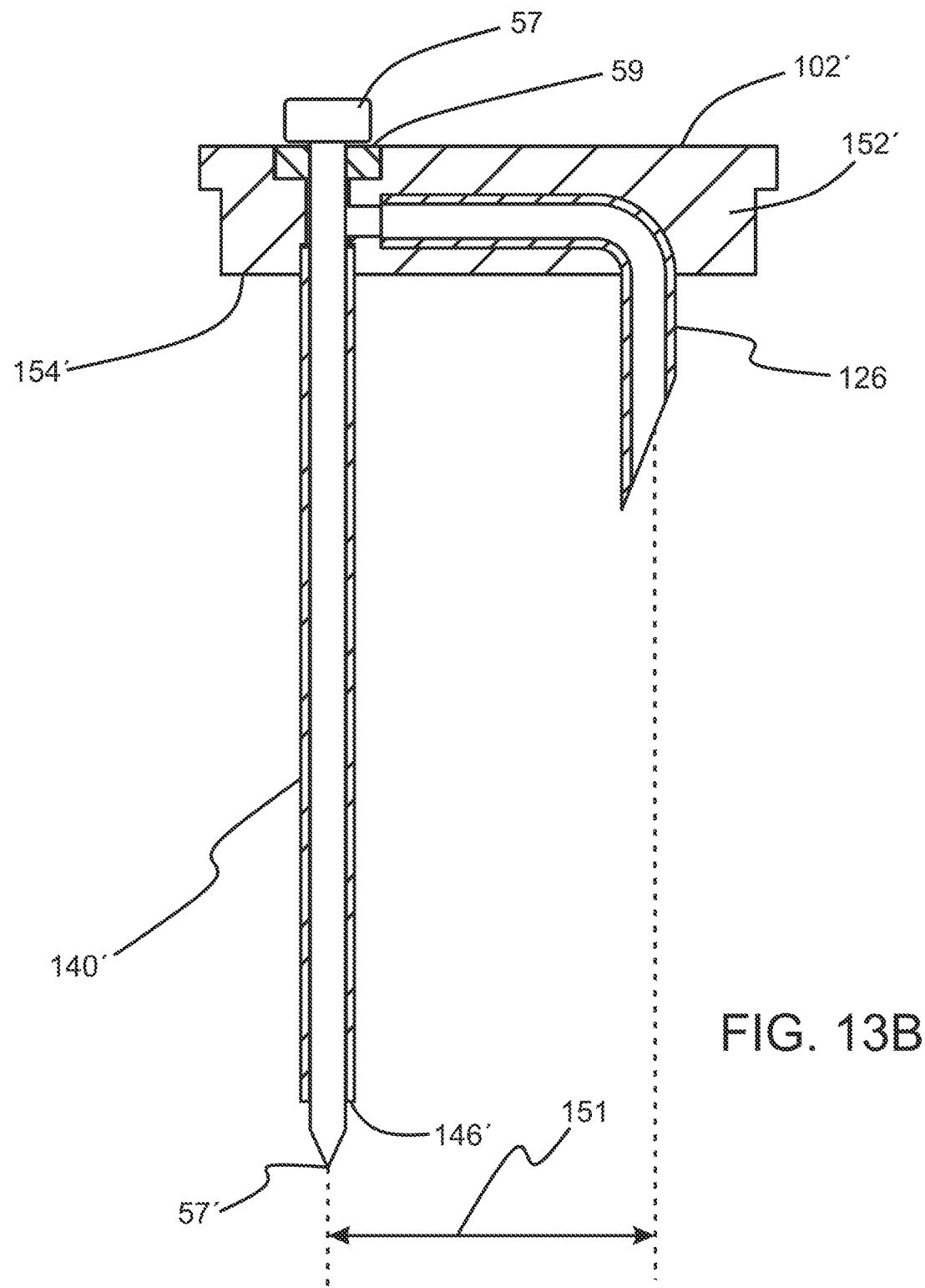
FIG. 13B is an elevation view in partial section of an access cannula set embodiment including a delivery cannula embodiment that includes a soft pliable hollow tubular structure and an inserter needle disposed within an inner lumen thereof.

Regarding supply cannula embodiments 126 and delivery cannula embodiments 140 discussed herein, in some cases the supply cannula embodiments 126 and delivery cannula embodiments 140 may include a rigid high strength structure that resists bending that may be made from a high strength material including biocompatible metallic alloys such as stainless steel, nickel titanium alloy or the like as shown as may be exemplified by the supply cannula embodiment 126 and delivery cannula embodiment 140 of FIG. 13A. In those embodiments, the sharpened tips 132, 148 may be integrally formed from the wall material of the tubular structure of the supply cannula 126 and delivery cannula 140. FIG. 13B shows a delivery cannula embodiment 140' wherein the hollow tubular structure of the delivery cannula 140' may be made from a soft pliable material such as polyurethane, polytetrafluoroethylene (PTFE) including expanded PTFE or the like. For such delivery cannula embodiments 140', the inserter needle 57 having a sharpened distal tip 57' that extends from a distal port 146' of the hollow tubular structure of the delivery cannula 140' may disposed within an inner lumen of the delivery cannula 140' during deployment of the delivery cannula 140' through a delivery cannula port 116 and/or the patient's tissue 24'. Once such a delivery cannula embodiment 140' is deployed, the inserter needle 57 may be proximally withdrawn from the inner lumen of the tubular structure of the delivery cannula 140'. In order to seal a shaft of the inserter needle 57, an inserter septum 59 may be disposed at and sealed across a proximal end of the tubular structure of the delivery cannula 140'. After the inserter needle 57 has been withdrawn post deployment of the delivery cannula 140', the passage formed by the inserter needle 57 in the inserter septum 59 will self-close due to the resilient and elastic nature of the material of the septum which may include any of the materials discussed herein with regard to any septum embodiments 30, 108, including rubber, polyurethane, polyisoprene, silicone or the like.

Figure 14C:
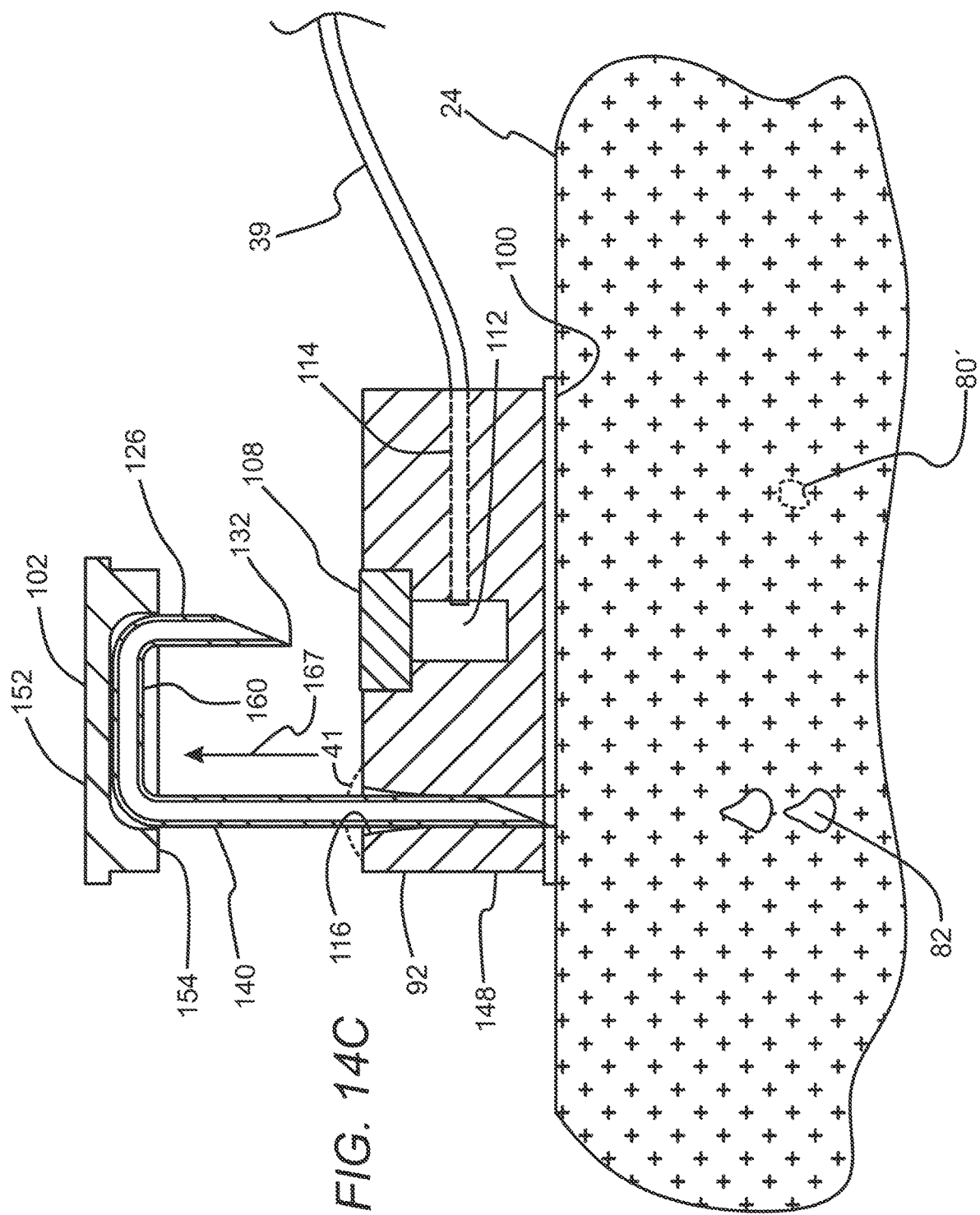

Referring to FIGS. 14A-14C, some embodiments of a method of accessing a plurality of subcutaneous positions 80 on a patient may include applying a contact surface 100 of an adhesive layer 98 of a housing 92 of a subcutaneous access hub embodiment 90 to an outer surface 24 of a patient's skin at a desired location as shown in FIG. 14A. Application of the contact surface 100 may serve to releasably secure the housing 92 to the outside surface 24 of the patient's skin at the desired location. Thereafter, the first delivery cannula 140 of the first access cannula set 102 of the subcutaneous access hub 90 may be deployed such that the sharpened tip 148 and distal port 146 of the first delivery cannula 140 is deployed in a first delivery cannula port 116 of a plurality of delivery cannula ports 116 of the housing 92. The deployment of the delivery cannula 140 further includes passing the hollow tubular structure of the first delivery cannula 140 through the first bore 118 of the first delivery cannula port 116 until the distal port 146 of the first delivery cannula 140 (which is disposed at the distal end 150 of the hollow tubular structure) is disposed at a first subcutaneous position 80 inward of the contact surface 100. The deployment of the first delivery cannula 140 may be carried out by axially translating the first delivery cannula 140 in an inward direction as indicated by arrow 165 of FIG. 14A. In some cases, deploying the first delivery cannula 140 as discussed above may include deploying the distal port 146 of the first delivery cannula 140 to a penetration depth 166 as shown in FIG. 14B of about 1 mm to about 8 mm from the contact surface 100 of the housing 92 at the first subcutaneous position 80.

The method may also include deploying the first supply cannula 126 of the first access cannula set 102 such that a sharpened tip 132 and inlet port 136 of the first supply cannula 126 penetrates through the septum 108 of the first supply cannula port 104 of the housing 92. The deployment and advancement of the first supply cannula 126 may also include advancing the first supply cannula 126 through the a bore 106 of the first supply cannula port 104 until the inlet port 136 of the first supply cannula 126 is disposed in fluid communication with the cavity 112 of the first supply cannula port 104. The cavity 112 is disposed in fluid communication with the supply passageway 114 of the housing 92. In addition, for the first access cannula set embodiment 102 shown, the inlet port 136 is disposed in fluid communication with the distal port 146 of the first delivery cannula 140. For embodiments of the subcutaneous access hub 90 that include an access cannula set 102 wherein the first delivery cannula 140 is secured in fixed relation to the first supply cannula 126, the first delivery cannula 140 may be deployed and inserted into the first delivery cannula port 116 simultaneously with deployment and insertion of the first supply cannula 126 into the first supply cannula port 104.

Thereafter, in some cases, a therapeutic fluid 82 may be delivered from the distal port 146 of the first delivery cannula 140 into the first subcutaneous position 80 prior to withdrawing the first delivery cannula 140 from the first subcutaneous position 80. In some cases, delivering the therapeutic fluid 82 from the distal port 146 of the first delivery cannula 140 into the first subcutaneous position 80 may include passing the therapeutic fluid 82 from the fluid source 38, through the supply conduit 39 which is in fluid communication with the supply passageway 114 of the housing 92 as indicated by the arrow disposed adjacent the supply conduit 39 in FIG. 14B. The therapeutic fluid 82 is also passed through the supply passageway 114 and into the cavity 112 of the first supply cannula port 104, then into the inlet port 136 of the first supply cannula 126 as indicated by the arrow in the supply passageway 114 in FIG. 14B. The therapeutic fluid 82 then passes through the inner lumen 130 of the hollow tubular structure of the first supply cannula 126, through the inner lumen 144 of the first delivery cannula 140 and then may be emitted out of the distal port 146 of the first delivery cannula 140 and into the patient's tissue at the first subcutaneous position 80 at a desired delivery site within the patient. In some cases, the fluid source 38 includes an insulin pump and the therapeutic fluid 82 comprises insulin.

After delivery of the therapeutic fluid 82 over any suitable desired number of cycles, volume dispensed, or period of time, the first delivery cannula 140 may be withdrawn by axially translating the first delivery cannula 140 in an outward direction from the first subcutaneous position 80 and the first delivery cannula port 116 of the housing 92 as indicated by arrow 167 in FIG. 14C. The first supply cannula 126 may also optionally be withdrawn from the supply cannula port 104 at this stage. A second delivery cannula 140 of a second access cannula set 102 may then be similarly deployed such that the sharpened tip 148 and distal port 146 of the corresponding second delivery cannula 140 passes through a second delivery cannula port 116' of a plurality of delivery cannula ports 116 of the housing 92. The deployment of the second delivery cannula 140 may further include passing the hollow tubular structure of the second delivery cannula 140 through a second bore 118 of the second delivery cannula port 116' until the distal port 146 of the second delivery cannula 140 is disposed at a second subcutaneous position 80' of the patient's body inward of the contact surface 100. In some cases, deploying the second delivery cannula 140 as discussed above may include deploying the distal port 146 of the second delivery cannula 140 to a penetration depth 166 of about 1 mm to about 8 mm from the contact surface 100 of the housing 92 at the second subcutaneous position 80'. Although it may be possible to reuse an access cannula set 102 in some cases, generally a new unused second access cannula set 102 will be used to access a second subcutaneous position 80' in a patient once a first access cannula set 102 has been used to access a first subcutaneous position 80. As such, the subcutaneous access hub embodiments 90 may include a plurality of access cannula sets 102, including about 2 access cannula sets 102 to about 20 access cannula sets 102 or more.

A second supply cannula 126 of a second access cannula set 102 may also then be deployed into the same supply cannula port 104 or an alternate different supply cannula port 104 depending on the configuration of the housing embodiment 92. For example, the housing embodiment 92" discussed above would permit a second supply cannula 126 of a second access cannula set 102 to be deployed into one of a plurality of second supply cannula ports 104 which are in different positions relative to the first supply cannula port 104.

Once the second access cannula set 102 has been deployed at a second subcutaneous position, a therapeutic fluid 82 may be delivered from the distal port 146 of the second delivery cannula 140 into the second subcutaneous position 80'. In some cases, delivering the therapeutic fluid 82 from the distal port 146 of the second delivery cannula 140 into the second subcutaneous position 80' may include passing the therapeutic fluid 82 from the fluid source 38, through the supply conduit 39 which is in fluid communication with the supply passageway 114 of the housing 92, through the supply passageway 114 and into the cavity 112 of the supply cannula port 104. The therapeutic fluid 82 may then pass into the inlet port 136 of the supply cannula 126. The therapeutic fluid 82 then passes through the inner lumen 130 of the hollow tubular structure of the supply cannula 126, through the inner lumen 144 of the second delivery cannula 140 and then may be emitted out of the distal port 146 of the second delivery cannula 140 and into the patient's tissue at the second subcutaneous position 80' at a desired delivery site within the patient. In some cases, the fluid source 38 includes an insulin pump and the therapeutic fluid 82 comprises insulin.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:
1. A subcutaneous access hub, comprising:
  a housing, including:
    an outer surface,
    an inner surface,
    an adhesive layer which is secured to the inner surface of the housing and which includes a contact surface that is configured to be releasably secured to an outside surface of a patient's skin,
a plurality of delivery cannula ports which are disposed at different positions on the housing, each delivery cannula port including:
a bore that extends from the outer surface to the inner surface of the housing, and
a septum which is disposed within and sealed across an outer portion of the bore and which includes a cavity which is disposed within the septum,
a supply passageway which is disposed on the housing and which is in fluid communication with the cavity of the septum of each of the plurality of delivery cannula ports; and
a delivery cannula, including:
a hollow tube with an outer contour configured to slide within the bore of each of the plurality of delivery cannula ports, a wall portion, a proximal end, a distal end, a sharpened tip disposed on the distal end, an inner lumen extending an axial length of the hollow tube, a distal port which is in fluid communication with the inner lumen and which is disposed at a distal end of the inner lumen, and an inlet port which is in fluid communication with the inner lumen and which is disposed at a proximal portion of the hollow tube,
an axial length of the delivery cannula sufficient for the sharpened tip and the distal port to extend below the contact surface of the adhesive layer when the inlet port is in fluid communication with the cavity of the septum of the delivery cannula port, and
a grip disposed on a proximal end of the hollow tube, the grip including a stop surface at a distal end of the grip, and wherein the inlet port of the hollow tube of the delivery cannula is disposed distally of the stop surface at a distance equal to or greater than a distance between the outer surface of the housing and the cavity of each respective septum so as to allow the distal port to achieve fluid communication between the cavity of each septum and the inlet port when the stop surface is disposed adjacent the outer surface of the housing.

2. The subcutaneous access hub of claim 1 wherein the plurality of delivery cannula ports of the housing and the delivery cannula are configured such that the distal port of the delivery cannula extends to a penetration depth of 1 mm to 8 mm from the contact surface when the delivery cannula is disposed within any of the plurality of delivery cannula ports with the stop surface adjacent the outer surface of the housing.

3. A subcutaneous access hub, comprising:
a housing, including:
an outer surface,
an inner surface,
an adhesive layer which is secured to the inner surface of the housing and which includes a contact surface that is configured to be releasably secured to an outside surface of a patient's skin,
a plurality of delivery cannula ports which are disposed at different positions on the housing, each delivery cannula port including:
a bore that extends from the outer surface to the inner surface of the housing, and
a septum which is disposed within and sealed across an outer portion of the bore and which includes a cavity which is disposed within the septum,
a supply passageway which is disposed on the housing and which is in fluid communication with the cavity of the septum of each of the plurality of delivery cannula ports; and
a delivery cannula, including:
a hollow tube with an outer contour configured to slide within the bore of each of the plurality of delivery cannula ports, a wall portion, a proximal end, a distal end, a sharpened tip disposed on the distal end, an inner lumen extending an axial length of the hollow tube, a distal port which is in fluid communication with the inner lumen and which is disposed at a distal end of the inner lumen, and an inlet port which is in fluid communication with the inner lumen and which is disposed at a proximal portion of the hollow tube,
an axial length of the delivery cannula sufficient for the sharpened tip and the distal port to extend below the contact surface of the adhesive layer when the inlet port is in fluid communication with the cavity of the septum of the delivery cannula port, and
wherein a transverse dimension of an outer surface of the delivery cannula comprises a close fit with an inner surface of the bore of each of the plurality of delivery cannula ports.

4. The subcutaneous access hub of claim 3 wherein a clearance between the outer surface of the delivery cannula and the inner surface of the bore of each of the plurality of delivery cannula ports is 0.5 percent to 5 percent of the transverse dimension of the delivery cannula.

5. A subcutaneous access hub, comprising:
a housing, including:
an outer surface,
an inner surface,
an adhesive layer which is secured to the inner surface of the housing and which includes a contact surface that is configured to be releasably secured to an outside surface of a patient's skin,
a plurality of delivery cannula ports which are disposed at different positions on the housing, each delivery cannula port including:
a bore that extends from the outer surface to the inner surface of the housing, and
a septum which is disposed within and sealed across an outer portion of the bore and which includes a cavity which is disposed within the septum,
a supply passageway which is disposed on the housing and which is in fluid communication with the cavity of the septum of each of the plurality of delivery cannula ports; and
a delivery cannula, including:
a hollow tube with an outer contour configured to slide within the bore of each of the plurality of delivery cannula ports, a wall portion, a proximal end, a distal end, a sharpened tip disposed on the distal end, an inner lumen extending an axial length of the hollow tube, a distal port which is in fluid communication with the inner lumen and which is disposed at a distal end of the inner lumen, and an inlet port which is in fluid communication with the inner lumen and which is disposed at a proximal portion of the hollow tube,
an axial length of the delivery cannula sufficient for the sharpened tip and the distal port to extend below the contact surface of the adhesive layer when the inlet port is in fluid communication with the cavity of the septum of the delivery cannula port, and
an inserter septum disposed and sealed across a proximal end of the inner lumen of the hollow tube and an inserter needle disposed within the inserter septum and the inner lumen of the hollow tube with a sharpened tip of the inserter needle extending from the distal port of the hollow tube.

\* \* \* \* \*